US007186726B2

(12) United States Patent
Snutch et al.

(10) Patent No.: US 7,186,726 B2
(45) Date of Patent: *Mar. 6, 2007

(54) PREFERENTIALLY SUBSTITUTED CALCIUM CHANNEL BLOCKERS

(75) Inventors: Terrance P. Snutch, Vancouver (CA); Gerald W. Zamponi, Cochrane (CA); Hassan Pajouhesh, Vancouver (CA); Hossein Pajouhesh, Burnaby (CA); Francesco Belardetti, Vancouver (CA)

(73) Assignee: Neuromed Pharmaceuticals Ltd., Vancouver (CA)

( * ) Notice: Subject to any disclaimer, the term of this patent is extended or adjusted under 35 U.S.C. 154(b) by 445 days.

This patent is subject to a terminal disclaimer.

(21) Appl. No.: 10/655,393

(22) Filed: Sep. 3, 2003

(65) Prior Publication Data

US 2004/0147529 A1    Jul. 29, 2004

Related U.S. Application Data

(63) Continuation-in-part of application No. 10/060,900, filed on Jan. 29, 2002, now Pat. No. 6,617,322, which is a continuation of application No. 09/476,927, filed on Dec. 30, 1999, now Pat. No. 6,387,897, which is a continuation-in-part of application No. 09/401,699, filed on Sep. 23, 1999, now Pat. No. 6,294,533, which is a continuation-in-part of application No. 09/107,037, filed on Jun. 30, 1998, now Pat. No. 6,011,035.

(51) Int. Cl.
*A61K 31/4965* (2006.01)
*C07D 295/00* (2006.01)

(52) U.S. Cl. .................. 514/255.01; 544/381; 544/391

(58) Field of Classification Search ................ None
See application file for complete search history.

(56) References Cited

U.S. PATENT DOCUMENTS

| 3,288,795 | A | 11/1966 | Irikura et al. ................ 260/268 |
| 4,188,485 | A | 2/1980 | Kukla .......................... 546/202 |
| 4,918,073 | A | 4/1990 | Rüger et al. .................. 514/255 |
| 5,386,025 | A | 1/1995 | Jay et al. ..................... 536/23.5 |
| 5,391,552 | A | 2/1995 | Inazu et al. |
| 5,428,038 | A | 6/1995 | Chatterjee et al. .......... 514/253 |
| 5,623,051 | A | 4/1997 | Catterall et al. ............. 530/324 |
| 5,646,149 | A | 7/1997 | Hellberg et al. ............. 514/253 |
| 5,703,071 | A | 12/1997 | Itoh et al. .................... 514/218 |
| 5,866,574 | A | 2/1999 | Okamura et al. |
| 6,011,035 | A | 1/2000 | Snutch et al. ............... 514/231.2 |
| 6,294,533 | B1 | 9/2001 | Snutch et al. ............... 514/231.2 |
| 6,310,059 | B1 | 10/2001 | Snutch ...................... 514/222.2 |
| 6,387,897 | B1 | 5/2002 | Snutch ...................... 514/231.2 |
| 6,458,781 | B1 | 10/2002 | Connor et al. |
| 6,492,375 | B2 | 12/2002 | Snutch |
| 6,617,322 | B2 * | 9/2003 | Snutch ...................... 514/231.2 |
| 6,943,168 | B2 * | 9/2005 | Snutch et al. .............. 514/252.13 |
| 6,949,554 | B2 * | 9/2005 | Snutch et al. .............. 514/252.13 |
| 6,951,862 | B2 * | 10/2005 | Snutch et al. .............. 514/255.01 |
| 2001/0029258 | A1 | 10/2001 | Snutch ...................... 514/231.2 |
| 2004/0034035 | A1 | 2/2004 | Snutch et al. .............. 514/255.01 |
| 2004/0147529 | A1 | 7/2004 | Snutch et al. |

FOREIGN PATENT DOCUMENTS

| BG | 17385 | 11/1973 |
| CA | 2335461 | 6/1999 |
| CA | 2394327 | 6/2001 |
| EP | 0 187 524 | 7/1986 |
| EP | 0 213 006 | 3/1987 |
| EP | 0 458387 | 11/1991 |
| EP | 0 496 691 | 7/1992 |
| ES | 504 202 | 1/1983 |
| ES | 514 167 | 4/1983 |
| ES | 8 304 135 | 5/1983 |
| ES | 8 305 343 | 7/1983 |
| GB | 920 416 | 3/1963 |
| GB | 1 513 883 | 6/1978 |
| WO | WO 94/14786 | 7/1994 |
| WO | WO-97/24328 | 7/1997 |
| WO | WO-99/06383 | 2/1999 |
| WO | WO 99/15129 | 4/1999 |
| WO | WO 99/25686 | 5/1999 |
| WO | WO 00/01375 | 1/2000 |
| WO | WO 00/18402 | 4/2000 |
| WO | WO 00/37059 | 6/2000 |
| WO | WO 01/45709 | 6/2001 |
| WO | WO-01/49670 | 7/2001 |
| WO | WO-03/068759 | 8/2003 |
| WO | WO-03/76421 | 9/2003 |

OTHER PUBLICATIONS

Cao et al., Journal of Medicinal Chemistry (1992) 46(13):2589-2598.
International Search Report for PCT/CA2005/000544, mailed on Aug. 24, 2005, 7 pages.
Korzycka et al., Polish Journal of Pharmacology and Pharmacy (1986) 38(5-6):545-553.
International Search Report for PCT/CA2004/000535, mailed on Jul. 1, 2004, 5 pages.
Invitation to Pay Additional Fees for PCT/CA2004/000539, mailed on Sep. 2, 2004, 6 pages.
Boger et al., Helvetica Chimica Acta (2000) 83(8):1825-1845.
International Search Report for PCT/CA2004/000539, mailed on Dec. 22, 2004, 9 pages.
International Search Report for PCT/CA2004/001629, mailed on Jan. 21, 2005, 6 pages.
Jamieson et al., Synlett (2000) 11:1603-1607.

(Continued)

*Primary Examiner*—Raymond J. Henley, III
(74) *Attorney, Agent, or Firm*—Morrison & Foerster LLP

(57) ABSTRACT

Certain piperazine substituted compounds are described which are useful in altering calcium channel activity.

18 Claims, 9 Drawing Sheets

OTHER PUBLICATIONS

Toldy et al., Acta Chimica Academiae Scientiarum Hungarica (1965) 44:301-325.

Webster et al., Journal of the Chemical Society (2001) 14:1673-1695.

Bourinet et al., "Splicing of $\alpha_{1A}$ Subunit Gene Generates Phenotypic Variants of P- and Q-Type Calcium Channels," *Nature Neuroscience* (1999) 2:407-415.

Chiarini, A. et al., "1,4-Dihydropyridines Bearing a Pharmacophoric Fragment of Lidoflazine," (1996). *Bioorg & Med Chemistry* 4(10):1629-1635.

Cohan et al., "Depolarization-Induced Presynaptic Calcium Accumulation May Occur by an N-Type Channel that is Blocked by Flunarizine," *Annals of the New York Academy of Sciences* (1991) 635:397-399.

Cribbs et al., "Cloning and Characterization of $\alpha$1H from Human Heart, A Member of the T-Type $Ca^{2+}$Channel Gene Family,"*Circulation Research* (1998) 83:103-109.

Database WPI Week 9711 Derwent Publications Ltd., London, GB; Abstract JP 09 003067, XP002133055 (Hisamitsu Pharm Co Ltd.) Jan. 7, 1997.

De Waard et al., "Structural and Functional Diversity of Voltage-Activated Calcium Channels," ION CHANNELS (Narahashi, T. ed. Plenum Press, NY 1997) 4:41-87.

Dhainaut et al., "New Triazine Derivatives as Potent Modulators of Multidrug Resistance," *J Med Chem* (1992) 35:2481-2496.

Dooley, "Lomerizine Kanebo KK" *Current Opinion in CPNS Investigational Drugs* (1999) 1(1):116-125.

Dunlap et al., "Exocytotic $Ca^{2+}$Channels in Mammalian Central Neurons," *Trends Neuroscience* (1995) 18:89-98.

Estep et al., "Synthesis and Structure-Activity Relationships of 6-Heterocyclic-Substituted Purines as Inactivation Modifiers of Cardiac Sodium Channels," *J Med Chem* (1995) 38:2582-2595.

Galizzi et al., "Neuroleptics of the Diphenylbutylpiperidine Series are Potent Calcium Channel Inhibitors," *Proc Natl Acad Sci USA* (1986) 83: 7513-7517.

Glamkowski et al., "Synthesis of 3-(4-Acylaminopiperazin-1-ylalkyl) Indoles as Potential Antihypertensive Agents," *J Med Chem* (1977) 20(11):1485-1489.

Gould et al., "Antischizophrenic Drugs of the Diphenylbutylpiperidine Type Act as Calcium Channel Antagonists," *Proc Natl Acad Sci* (1983) 80:5122-5125.

Grantham et al., "Fluspirilene Block of N-Type Calcium Current in NGF-Differentiated PC12 Cells," *Brit J Pharmacol* (1994) 111:438-488.

Ito et al., "U-92032, a T-Type $Ca^+$Channel Blocker and Antioxidant, Reduces Neuronal Ischemic Injuries," *Eur J Pharmacol* (1994) 257:203-210.

King et al., "Substituted Diphenylbutylpiperidines Bind to a Unique High Affinity Site on the L-Type Calcium Channel," *J Biol Chem* (1989) 264:5633-5641.

Lee et al., "Cloning and Expression of a Novel Member of the Low Voltage-Activated T-Type Calcium Channel Family," *J of Neurosci* (1999) 19:1912-1921.

Lehmann et al., "Zur Struktur und Pharmakologies γ-lactonverbruckter Diphenylalkylamine," *Arch Pharm* (1988) 321:807-812.

"Lomerizine Kanebo KK," published in Current Opinion in CPNS Investigational Drugs (1999) 1(1):116-125.

McCleskey et al., "Functional Properties of Voltage Dependent Calcium Channels," *Curr Topics* (1991) 39:295-326.

Miyano et al., "The Synthesis and Antilipidperoxidation Activity of 4,4-diarylbutylamines and 4,4-diarylbutanamides," *Chem Pharm Bull* (1990) 38(6):1570-1574.

Ohtaka et al., "Benzylpiperazine Derivatives. V. Quantitative Structure-Activity Relationships of 1-Benzyl-4-diphenylmethylpiperazine Derivatives for Cerebral Vasodilating Activity," *Chem Pharm Bull* (1987) 35(10):4117-4123.

Ohtaka et al., "Benzylpiperazine Derivatives. IV. Syntheses and Cerebral Vasodilating Activities of 1-Benzyl-4-diphenylmethyl-piperazine Derivatives," *Chem Pharm Bull* (1987) 35(8):3270-3275.

Perez-Reyes et al., "Molecular Characterization of a Neuronal Low-Voltage-Activated T-Type Calcium Channel," *Nature* (1998) 391:896-900.

Prasad et al., "Potential Antihypertensive Agents. II. Unsymmetrically 1.4-disubstituted Piperazines," *J Med Chem* (1968) 11(6):1144-1150.

Sather et al., "Distinctive Biophysical and Pharmacological Properties of Class A (BI) Calcium Channel $\alpha_1$ Subunits," *Neuron* (1993) 11:291-303.

Stea et al., "Localization and Functional Properties of a Rat Brain $\alpha_{1A}$ Calcium Channel Reflect Similarities to Neuronal Q- and P-Type Channels," Proc Natl Acad Sci USA (1994) 91:10576-10580.

Stea et al., Handbook of Receptors and Channels (North, R.A. ed. CRC Press 1995) 113-151.

Tytgat et al., "Flunarizine Inhibits a High-threshold Inactivating Calcium Channel (N-type) in Isolated Hippocampal Neurons," *Brain Research* (1991) 549:112-117.

Uneyama et al., "Non-L-type Actions of Organic $Ca^{2+}$ Channel Blockers: Implications for $Na^+$and N-type $Ca^{2+}$Channels Blockades," *Calcium Ion Modulators, Sel Pap Satell Symp* (1988) 13-23.

Vadodaria et al., "Synthesis and Central Nervous System Depressant Activity of New Piperazine Derivatives and Related Compounds. II," *J Med Chem* (1969) 12:860-865.

Zikolova et al., "Analogs of N1-benzhydryl-N4-cinnamylpiperazine (cinnarizine). II. N1-substituted-N4-benzhydrylpiperazines," *Tr Nauchnoizsled Khim—Farm Inst* (1972) 8:59-67 (Database Chemabs 'Online! Chemical Abstracts Service, Columbus, Ohio, AN: 78:147908, XP002133054).

Zikolova et al., "Analogs of 1N-benzhydryl-4N-cinnamylpiperazine (cinnarizine). V. New N1-benzhydryl-N4-substituted Piperazines," *Tr Nauchnoizsled Khim—Farm Inst* (1984) 14:23-28 (Database Chemabs 'Online! Chemical Abstracts Service, Columbus, Ohio, AN: 103:37454, XP002133053).

Lima and Barreiro, Curr. Med. Chem. (2005) 12:23-49.

Written Opinion of the International Preliminary Examining Authority for PCT/CA2005/000544, mailed on Jun. 20, 2006, 7 pages.

* cited by examiner

| Compound Number | Name | Structure |
|---|---|---|
| P1 | 1-{4-[4-(4-Fluoro-benzyl)-phenyl]-piperazin-1-yl}-3,3-diphenyl-propan-1-one | 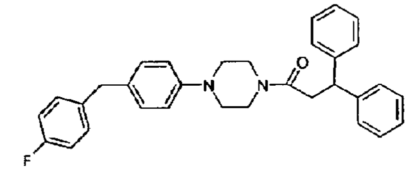 |
| P2 | 1-[4-(3,5-Di-tert-butyl-4-hydroxy-benzyl)-piperazin-1-yl]-3,3-diphenyl-propan-1-one | 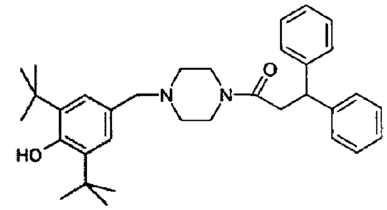 |
| P3 | 1-{4-[3-(4-Amino-2,3,5-trimethyl-phenoxy)-2-hydroxy-propyl]-piperazin-1-yl}-3,3-diphenyl-propan-1-one | 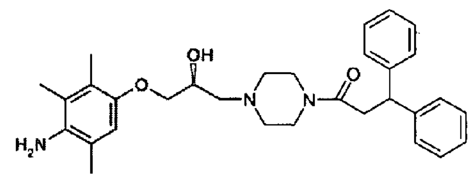 |
| P4 | 1-(4-Adamantan-1-ylmethyl-piperazin-1-yl)-3,3-diphenyl-propan-1-one | 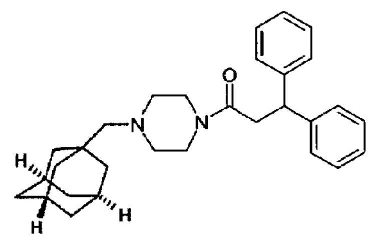 |
| P5 | 1-(4-Benzothiazol-2-yl-piperazin-1-yl)-3,3-diphenyl-propan-1-one | 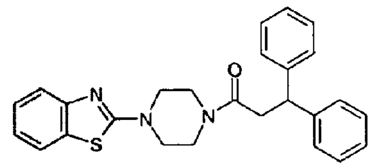 |
| P6 | 3,3-Diphenyl-1-{4-[2-(3,4,5-trimethoxy-phenoxy)-ethyl]-piperazin-1-yl}-propan-1-one | 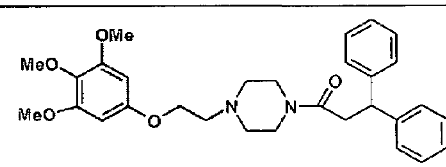 |
| P7 | 1-{4-[2-(3,4-Dimethoxy-phenoxy)-ethyl]-piperazin-1-yl}-3,3-diphenyl-propan-1-one | 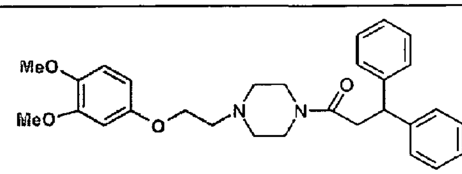 |

Figure 1 - 1

| Compound Number | Name | Structure |
|---|---|---|
| P8 | 1-{4-[2-(Benzothiazol-2-ylsulfanyl)-ethyl]-piperazin-1-yl}-3,3-diphenyl-propan-1-one | 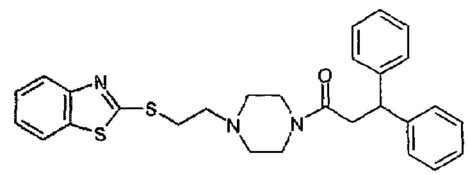 |
| P9 | N-(2,6-Dimethyl-phenyl)-2-[4-(3,3-diphenyl-propionyl)-piperazin-1-yl]-acetamide | 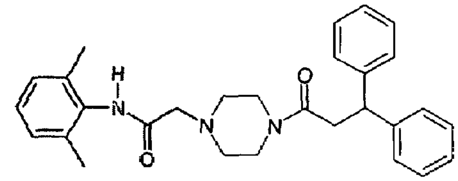 |
| P10 | 2-[4-(3,3-Diphenyl-propionyl)-piperazin-1-yl]-N-methyl-N-phenyl-acetamide | 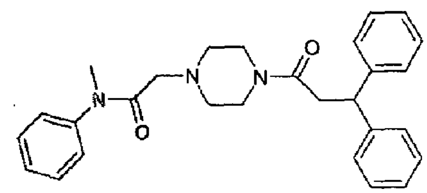 |
| P11 | 3,3-Diphenyl-1-[4-(1-phenyl-ethyl)-piperazin-1-yl]-propan-1-one | 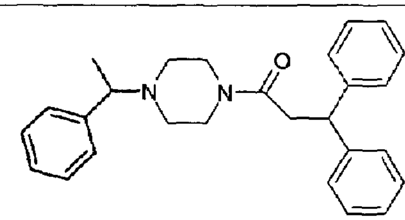 |
| P12 | 1-[4-(2-Diallylamino-ethyl)-piperazin-1-yl]-3,3-diphenyl-propan-1-one | 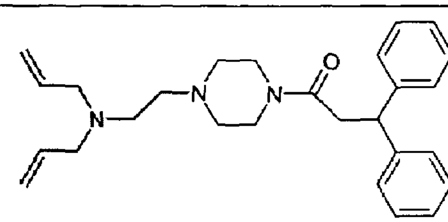 |
| P13 | 1-[4-(2-Dipropylamino-ethyl)-piperazin-1-yl]-3,3-diphenyl-propan-1-one | 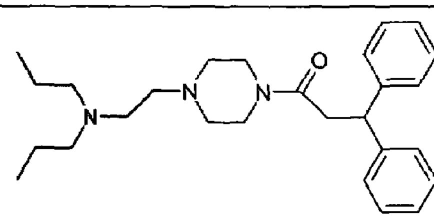 |

Figure 1 - 2

| Compound Number | Name | Structure |
|---|---|---|
| P14 | 1-(4-sec-Butyl-piperazin-1-yl)-3,3-diphenyl-propan-1-one | 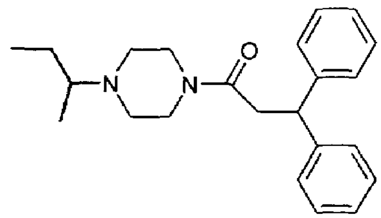 |
| P15 | 1-[4-(1-Ethyl-propyl)-piperazin-1-yl]-3,3-diphenyl-propan-1-one | 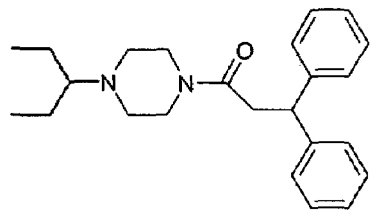 |
| P16 | 1-[4-(1-Methyl-piperidin-3-ylmethyl)-piperazin-1-yl]-3,3-diphenyl-propan-1-one | 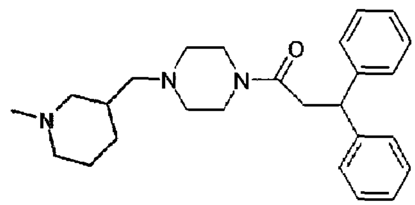 |
| P17 | 1-(4-Heptyl-piperazin-1-yl)-3,3-diphenyl-propan-1-one | 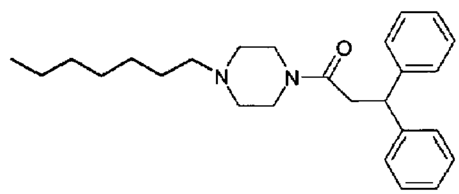 |
| P18 | 3,3-Diphenyl-1-(4-pyridin-4-ylmethyl-piperazin-1-yl)-propan-1-one | 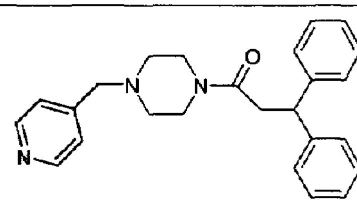 |
| P19 | 1-[4-(3,5-Dichloro-phenyl)-piperazin-1-yl]-3,3-diphenyl-propan-1-one | 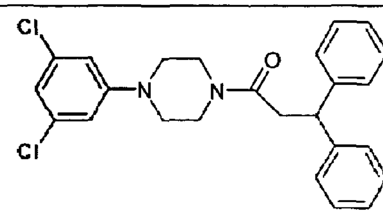 |

Figure 1 - 3

| Compound Number | Name | Structure |
|---|---|---|
| P20 | 1-(4-Cycloheptyl-piperazin-1-yl)-3,3-diphenyl-propan-1-one | 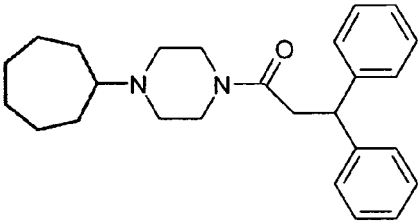 |
| P21 | 1-[4-(3,4-Dimethyl-phenyl)-piperazin-1-yl]-3,3-diphenyl-propan-1-one | 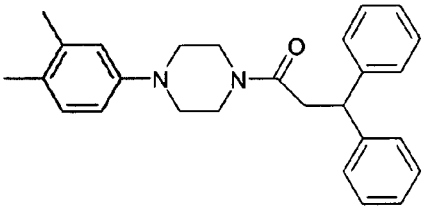 |
| P22 | 1-(4-Biphenyl-4-yl-piperazin-1-yl)-3,3-diphenyl-propan-1-one | 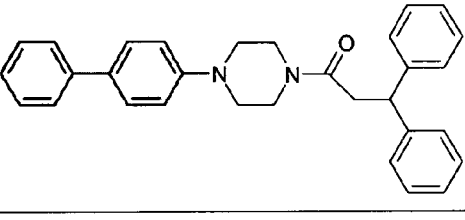 |
| P23 | 1-[4-(2,3-Dichloro-phenyl)-piperazin-1-yl]-3,3-diphenyl-propan-1-one | 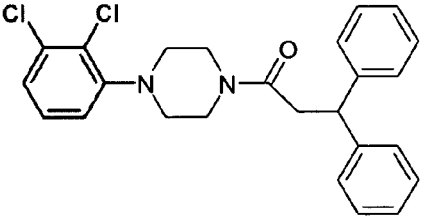 |
| P24 | 1-[4-(1-Methyl-piperidin-4-ylmethyl)-piperazin-1-yl]-3,3-diphenyl-propan-1-one | 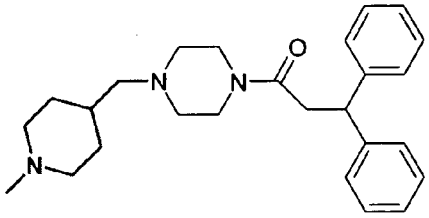 |
| P25 | N-{2-[4-(3,3-Diphenyl-propionyl)-piperazin-1-yl]-ethyl}-3,4,5-trimethoxy-benzamide | 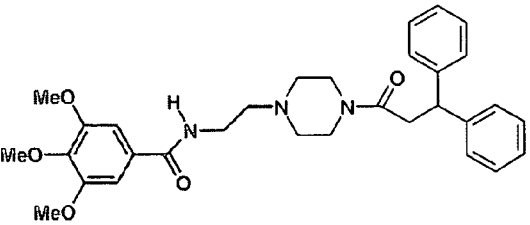 |
Figure 1 - 4

| Compound Number | Name | Structure |
|---|---|---|
| P26 | 1-(4-Naphthalen-1-ylmethyl-piperazin-1-yl)-3,3-diphenyl-propan-1-one | 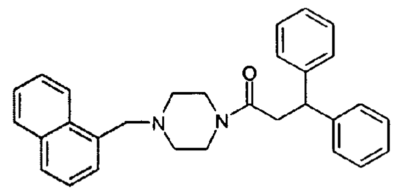 |
| P27 | 1-(4-Isopropyl-piperazin-1-yl)-3,3-diphenyl-propan-1-one | 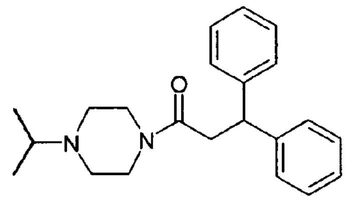 |
| P28 | 1-[4-(3-Dimethylamino-propyl)-piperazin-1-yl]-3,3-diphenyl-propan-1-one | 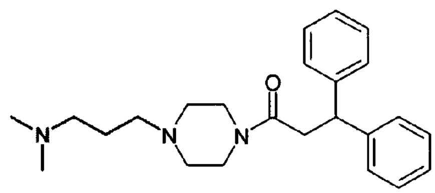 |
| P29 | 3,3-Diphenyl-1-[4-(4-trimethylsilanyl-phenyl)-piperazin-1-yl]-propan-1-one | 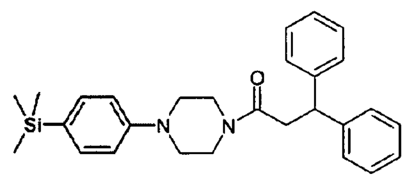 |
| P30 | 3,3-Diphenyl-1-[4-(2-phenylamino-ethyl)-piperazin-1-yl]-propan-1-one | 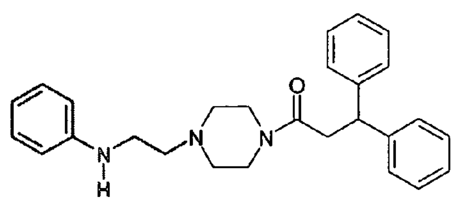 |
| P31 | 1-{4-[2-(2,4-Difluoro-phenoxy)-ethyl]-piperazin-1-yl}-3,3-diphenyl-propan-1-one | 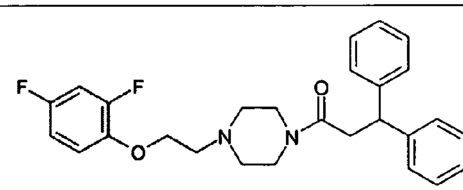 |
| P32 | 3,3-Diphenyl-1-{4-[2-(2,3,5,6-tetrafluoro-phenoxy)-ethyl]-piperazin-1-yl}-propan-1-one | 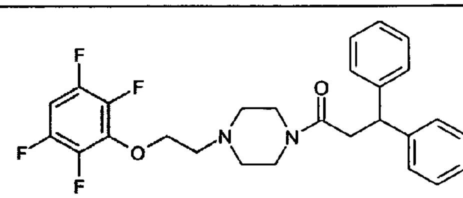 |

Figure 1 - 5

| Compound Number | Name | Structure |
|---|---|---|
| P33 | 1-[4-(1-Benzyl-1H-benzoimidazol-2-yl)-piperazin-1-yl]-3,3-diphenyl-propan-1-one | 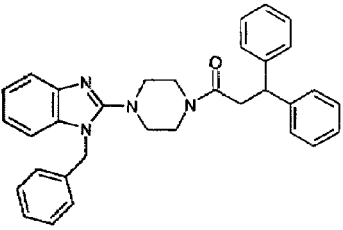 |
| P34 | 3,3-Diphenyl-1-[4-(phenyl-thiophen-2-yl-methyl)-piperazin-1-yl]-propan-1-one | 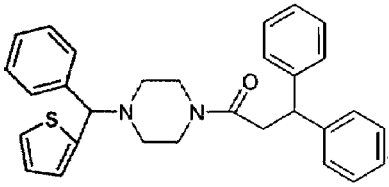 |
| P35 | 1-{4-[Cyclopropyl-(4-fluoro-phenyl)-methyl]-piperazin-1-yl}-3,3-diphenyl-propan-1-one | 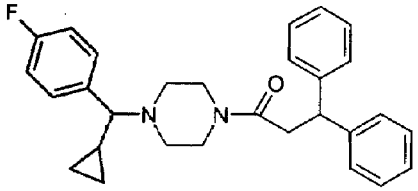 |
| P36 | (4-{2-[4-(3,3-Diphenyl-propionyl)-piperazin-1-yl]-ethoxy}-2,3,6-trimethyl-phenyl)-carbamic acid tert-butyl ester | 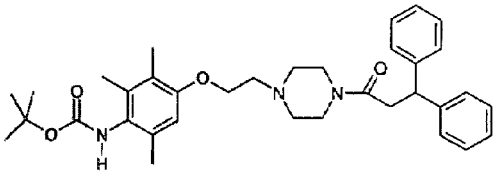 |
| P37 | 1-{4-[2-(4-Amino-2,3,5-trimethyl-phenoxy)-ethyl]-piperazin-1-yl}-3,3-diphenyl-propan-1-one | 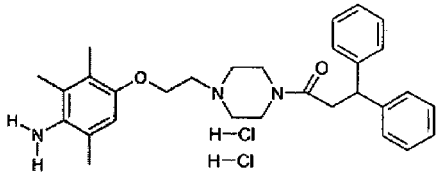 |
| P38 | 1-{4-[2-(4-Methoxy-phenoxy)-ethyl]-piperazin-1-yl}-3,3-diphenyl-propan-1-one | 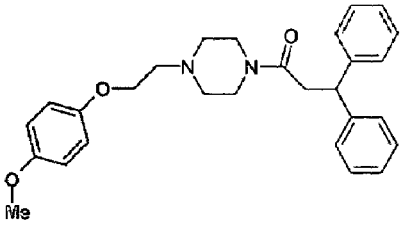 |

Figure 1 - 6

| Compound Number | Name | Structure |
|---|---|---|
| P39 | 1-{4-[2-(Benzo[1,3]dioxol-5-yloxy)-ethyl]-piperazin-1-yl}-3,3-diphenyl-propan-1-one | 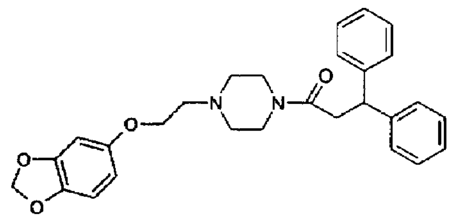 |
| P40 | 1-{4-[2-(2,4-Dichloro-phenoxy)-ethyl]-piperazin-1-yl}-3,3-diphenyl-propan-1-one | 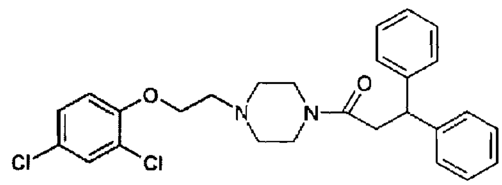 |
| P41 | 1-{4-[2-(4-Fluoro-phenoxy)-ethyl]-piperazin-1-yl}-3,3-diphenyl-propan-1-one | 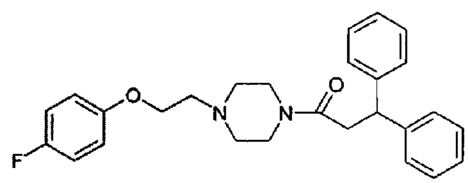 |
| P42 | 3,3-Diphenyl-1-[4-(2-phenylsulfanyl-ethyl)-piperazin-1-yl]-propan-1-one | 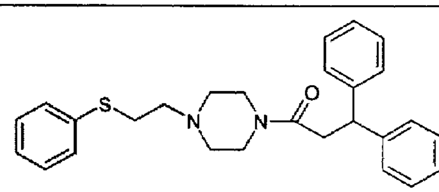 |

Figure 1 - 7

P/Q-type IC$_{50}$ = 6446 ± 3877 (6) nM

N-type IC$_{50}$ = 214 ± 39 (5) nM

L-type IC$_{50}$ = 19975 ± 7056 (5) nM

PREFERENTIALLY SUBSTITUTED CALCIUM CHANNEL BLOCKERS

CROSS-REFERENCE TO RELATED APPLICATIONS

This application is a continuation-in-part of U.S. Ser. No. 10/060,900 filed 29 Jan. 2002 now U.S. Pat. No. 6,617,322 which is a continuation of U.S. Ser. No. 09/476,927 filed 30 Dec. 1999, now U.S. Pat. No. 6,387,897; which is a continuation-in-part of U.S. Ser. No. 09/401,699, filed 23 Sep. 1999, now U.S. Pat. No. 6,294,533; which is a continuation-in-part of U.S. Ser. No. 09/107,037 filed 30 Jun. 1998, now U.S. Pat. No. 6,011,035. The contents of these applications are incorporated herein by reference.

TECHNICAL FIELD

The invention relates to compounds useful in treating conditions associated with abnormal calcium channel function. More specifically, the invention concerns compounds containing substituted or unsubstituted derivatives of 6-membered heterocyclic moieties that are useful in treatment of conditions such as stroke and pain.

BACKGROUND ART

PCT publication WO 01/45709 published 28 Jun. 2001 discloses calcium channel blockers where a piperidine or piperazine ring links a benzhydril moiety to an additional aromatic moiety or benzhydril. This publication, which is based on parent application Ser. No. 09/476,927, discussed above, is incorporated herein by reference. As explained in these applications, native calcium channels have been classified by their electrophysiological and pharmacological properties as T, L, N, P and Q types. T-type (or low voltage-activated) channels describe a broad class of molecules that transiently activate at negative potentials and are highly sensitive to changes in resting potential. The L, N, P and Q-type channels activate at more positive potentials (high voltage activated) and display diverse kinetics and voltage-dependent properties. There is some overlap in biophysical properties of the high voltage-activated channels, consequently pharmacological profiles are useful to further distinguish them. Whether the Q- and P-type channels are distinct molecular entities is controversial. Several types of calcium conductances do not fall neatly into any of the above categories and there is variability of properties even within a category suggesting that additional calcium channels subtypes remain to be classified.

Biochemical analyses show that neuronal high voltage activated calcium channels are heterooligomeric complexes consisting of three distinct subunits ($\alpha_1$, $\alpha_2\delta$ and $\beta$). The $\alpha_1$ subunit is the major pore-forming subunit and contains the voltage sensor and binding sites for calcium channel antagonists. The mainly extracellular $\alpha_2$ is disulfide-linked to the transmembrane $\delta$ subunit and both are derived from the same gene and are proteolytically cleaved in vivo. The $\beta$ subunit is a nonglycosylated, hydrophilic protein with a high affinity of binding to a cytoplasmic region of the $\alpha_1$ subunit. A fourth subunit, $\gamma$, is unique to L-type calcium channels expressed in skeletal muscle T-tubules.

Recently, each of these $\alpha_1$ subtypes has been cloned and expressed, thus permitting more extensive pharmacological studies. These channels have been designated $\alpha_{1A}$–$\alpha_{1I}$ and $\alpha_{1S}$ and correlated with the subtypes set forth above. $\alpha_{1A}$ channels are of the P/Q type; $\alpha_{1B}$ represents N; $\alpha_{1C}$, $\alpha'_{1D}$, $\alpha_{1F}$ and $\alpha_{1S}$ represent L; $\alpha_{1E}$ represents a novel type of calcium conductance, and $\alpha_{1G}$–$\alpha_{1I}$ represent members of the T-type family.

Further details concerning the function of N-type channels, which are mainly localized to neurons, have been disclosed, for example, in U.S. Pat. No. 5,623,051, the disclosure of which is incorporated herein by reference. As described, N-type channels possess a site for binding syntaxin, a protein anchored in the presynaptic membrane. Blocking this interaction also blocks the presynaptic response to calcium influx. Thus, compounds that block the interaction between syntaxin and this binding site would be useful in neural protection and analgesia. Such compounds have the added advantage of enhanced specificity for presynaptic calcium channel effects.

U.S. Pat. No. 5,646,149 describes calcium channel antagonists of the formula A-Y-B wherein B contains a piperazine or piperidine ring directly linked to Y. An essential component of these molecules is represented by A, which must be an antioxidant; the piperazine or piperidine itself is said to be important. The exemplified compounds contain a benzhydril substituent, based on known calcium channel blockers (see below). In some cases, the antioxidant can be a phenyl group containing methoxy and/or hydroxyl substituents. In most of the illustrative compounds, however, a benzhydril moiety is coupled to the heterocycle simply through a CH group or C= group. In the few compounds where there is an alkylene chain between the CH to which the two phenyl groups are bound and the heterocycle, the antioxidant must be coupled to the heterocycle through an unsubstituted alkylene and in most of these cases the antioxidant is a bicyclic system. Where the antioxidant can simply be a phenyl moiety coupled through an alkynylene, the linker from the heterocycle to the phenyl moieties contains no more than six atoms in the chain. U.S. Pat. No. 5,703,071 discloses compounds said to be useful in treating ischemic diseases. A mandatory portion of the molecule is a tropolone residue; among the substituents permitted are piperazine derivatives, including their benzhydril derivatives. U.S. Pat. No. 5,428,038 discloses compounds which are said to exert a neural protective and antiallergic effect. These compounds are coumarin derivatives which may include derivatives of piperazine and other six-membered heterocycles. A permitted substituent on the heterocycle is diphenylhydroxymethyl. Thus, approaches in the art for various indications which may involve calcium channel blocking activity have employed compounds which incidentally contain piperidine or piperazine moieties substituted with benzhydril but mandate additional substituents to maintain functionality.

Certain compounds containing both benzhydril moieties and piperidine or piperazine are known to be calcium channel antagonists and neuroleptic drugs. For example, Gould, R. J., et al., *Proc Natl Acad Sci USA* (1983) 80:5122–5125 describes antischizophrenic neuroleptic drugs such as lidoflazine, fluspirilene, pimozide, clopimozide, and penfluridol. It has also been shown that fluspirilene binds to sites on L-type calcium channels (King, V. K. et al. *J Biol Chem* (1989) 264:5633–5641) as well as blocking N-type calcium current (Grantham, C. J. et al. *Brit J Pharmacol* (1944) 111:483–488). In addition, Lomerizine, as developed by Kanebo KK, is a known calcium channel blocker; Lomerizine is, however, not specific for N-type channels. A review of publications concerning Lomerizine is found in Dooley, D., *Current Opinion in CPNS Investigational Drugs* (1999) 1:116–125.

In addition, benzhydril derivatives of piperidine and piperazine are described in PCT publication WO 00/01375 published 13 Jan. 2000 and incorporated herein by reference. This PCT publication corresponds to parent application Ser. No. 09/401,699 set forth above. Reference to this type of compound as known in the prior art is also made in WO 00/18402 published 6 Apr. 2000 and in Chiarini, A., et al., *Bioorganic and Medicinal Chemistry,* (1996) 4:1629–1635.

Various other piperidine or piperazine derivatives containing aryl substituents linked through nonaromatic linkers are described as calcium channel blockers in U.S. Pat. No. 5,292,726; WO 99/43658; Breitenbucher, J. G., et al., *Tat Lett* (1998) 39:1295–1298.

The present invention provides additional compounds which comprise benzhydril coupled to an acetyl group in turn coupled to a piperazine ring. The piperazine ring is, in turn, substituted by a variety of substituents, none of them antioxidants. These compounds are effective in blocking calcium ion channels.

DISCLOSURE OF THE INVENTION

The invention relates to compounds useful in treating conditions such as stroke, head trauma, migraine, chronic, neuropathic and acute pain, epilepsy, hypertension, cardiac arrhythmias, and other indications associated with calcium metabolism, including synaptic calcium channel-mediated functions. The compounds of the invention are benzhydril derivatives of piperazine with substituents that enhance the calcium channel blocking activity of the compounds.

Thus, in one aspect, the invention is directed to compounds of the formula

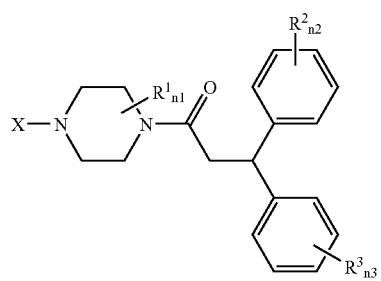

(1)

wherein each $R^1$–$R^3$ is independently a non-interfering substituent;

wherein a combination of $R^2$ and $R^3$ may form a bridge between phenyl groups which may be a bond, a $CR_2$ group, an NR group, O, or S wherein the S is optionally oxidized;

$n^1$ is 0–4 and $n^2$ and $n^3$ are independently 0–5; and wherein X is selected from the group consisting of:

(a) alkyl (1–12C) or alkenyl (2–12C) optionally including one or more N, O or S with the proviso that any N included in a ring is secondary or is tertiary solely because of an alkyl substitution;

(b) aryl, provided that if aryl is phenyl or pyridyl, said aryl must contain at least one substituent and wherein if said aryl is phenyl and contains only one substituent, said substituent must comprise an aryl group or a trialkylsilyl group and wherein said phenyl is not 2,3-dimethylphenyl or fused to an aliphatic ring;

(c) CRH-aryl wherein R is H, alkyl, or a heteroaromatic ring, wherein when R is H, aryl is optionally substituted 4-pyridyl, or is substituted phenyl other than phenyl fused to an aliphatic ring, or is substituted naphthyl or is substituted 5-membered aryl; and (d) alkylene-aryl wherein said alkylene contains at least 2 C, and further optionally contains one heteroatom and/or is substituted by =O and/or OH provided that if said alkylene is $CH_2CH_2$, $CH_2CH_2CH_2$, $CH_2CH_2O$ or $CH_2CH_2CH_2O$, and said aryl is phenyl, said phenyl must be substituted; and if said alkylene is $CH_2CH_2CH_2O$ substituted by OH, said aryl is other than substituted quinolyl or monosubstituted phenyl.

Non-interfering substituents are, generally, optionally substituted alkyl (1–12C), alkenyl (2–12C), alkynyl (2–12C), aryl (6–12C) or arylalkyl, arylalkenyl or arylalkynyl (each 7–16C) wherein in each of the foregoing 1–4C may be replaced by a heteroatom (Si, N, O and/or S) and wherein said optional substituents may include =O. When alkyl, alkenyl, or alkynyl comprises at least one cyclic moiety, the number of C contained may be as many as 15, again wherein one or more C may be replaced by a heteroatom. Thus, for example, $R^1$–$R^3$ may independently be in the form of an acyl, amide, or ester linkage with the ring carbon to which it is bound.

"Non-interfering substituents" also include halo, $CF_3$, $OCF_3$, CN, $NO_2$, $NR_2$, OR, SR, COOR, or $CONR_2$, wherein R is H or optionally substituted alkyl, alkenyl, alkynyl, aryl, or arylalkyl as described above. Two substituents at adjacent positions on the same ring may form a 3–7 membered saturated or unsaturated ring fused to said substituted ring, said fused ring optionally itself substituted and optionally contains one or more heteroatoms (N, S, O). $R^1$ may be keto if $n^1$ is 1 or 2.

The invention is also directed to methods to modulate calcium channel activity, preferably N-type and/or T-type channel activity, using the compounds of formula (1) and thus to treat certain undesirable physiological conditions; these conditions are associated with abnormal calcium channel activity. In another aspect, the invention is directed to pharmaceutical compositions containing these compounds, and to the use of these compounds for the preparation of medicaments for the treatment of conditions requiring modulation of calcium channel activity.

BRIEF DESCRIPTION OF THE DRAWINGS

FIGS. 1-1 to 1-7 show illustrative compounds of the invention.

FIG. 2 is a graph showing the selectivity of compound P24 of the invention for N-type, P/Q-type and L-type channels.

FIG. 3 is a graph showing the selectivity of compound P28 of the invention for N-type, P/Q-type and L-type channels.

MODES OF CARRYING OUT THE INVENTION

Figure 2:
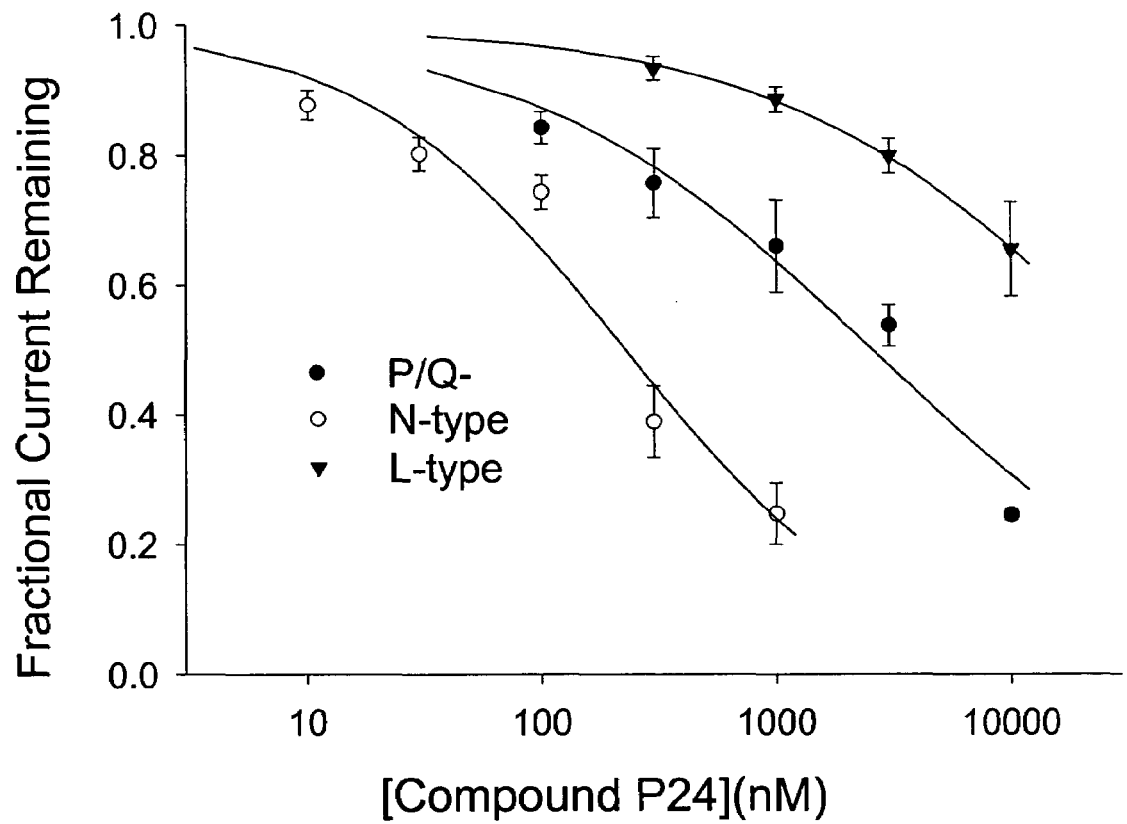

The compounds of formula (1) useful in the methods of the invention exert their desirable effects through their ability to modulate the activity of N-type and/or T-type calcium channels. This makes them useful for treatment of certain conditions. Among such conditions where antagonist activity is desired are stroke, epilepsy, head trauma, migraine, inflammatory bowel disease and chronic, neuropathic and acute pain. Calcium flux is also implicated in other neurological disorders such as schizophrenia, anxiety, depression, other psychoses, and neural degenerative disorders. Other treatable conditions include cardiovascular conditions such as hypertension and cardiac arrhythmias. In addition, T-type calcium channels have been implicated in certain types of cancer, diabetes, infertility and sexual dysfunction.

While the compounds of formula (1) generally have this activity, availability of this class of calcium channel modulators permits a nuanced selection of compounds for particular disorders. The availability of this class of compounds provides not only a genus of general utility in indications that are affected by excessive calcium channel activity, but also provides a large number of compounds which can be mined and manipulated for specific interaction with particular forms of calcium channels. The availability of recombinantly produced calcium channels of the $\alpha_{1A}$–$\alpha_{1I}$ and $\alpha_{1S}$ types set forth above, facilitates this selection process. Dubel, S. J., et al., *Proc Natl Acad Sci USA* (1992) 89:5058–5062; Fujita, Y., et al., *Neuron* (1993) 10:585–598; Mikami, A., et al., *Nature* (1989) 340:230–233; Mori, Y., et al., *Nature* (1991) 350:398–402; Snutch, T. P., et al., *Neuron* (1991) 7:45–57; Soong, T. W., et al., *Science* (1993) 260:1133–1136; Tomlinson, W. J., et al., *Neuropharmacology* (1993) 32:1117–1126; Williams, M. E., et al., *Neuron* (1992) 8:71–84; Williams, M. E., et al., *Science* (1992) 257:389–395; Perez-Reyes, et al., *Nature* (1998) 391:896–900; Cribbs, L. L., et al., *Circulation Research* (1998) 83:103–109; Lee, J. H., et al., *Journal of Neuroscience* (1999) 19:1912–1921.

It is known that calcium channel activity is involved in a multiplicity of disorders, and particular types of channels are associated with particular conditions. The association of N-type channels in conditions associated with neural transmission would indicate that compounds of the invention which target N-type channels are most useful in these conditions. Many of the members of the genus of compounds of formula (1) exhibit high affinity for N-type channels and/or T-type channels. Thus, as described below, they are screened for their ability to interact with N-type and T-type channels as an initial indication of desirable function. It is desirable that the compounds exhibit $IC_{50}$ values of <1 µM. The $IC_{50}$ is the concentration which inhibits 50% of the calcium flux at a particular applied potential.

There are two distinguishable types of calcium channel inhibition. The first, designated "open channel blockage," is conveniently demonstrated when displayed calcium channels are maintained at an artificially negative resting potential of about −100 mV (as distinguished from the typical endogenous resting maintained potential of about −70 mV). When the displayed channels are abruptly depolarized under these conditions, calcium ions are caused to flow through the channel and exhibit a peak current flow which then decays. Open channel blocking inhibitors diminish the current exhibited at the peak flow and can also accelerate the rate of current decay.

This type of inhibition is distinguished from a second type of block, referred to herein as "inactivation inhibition." When maintained at less negative resting potentials, such as the physiologically important potential of −70 mV, a certain percentage of the channels may undergo conformational change, rendering them incapable of being activated—i.e., opened—by the abrupt depolarization. Thus, the peak current due to calcium ion flow will be diminished not because the open channel is blocked, but because some of the channels are unavailable for opening (inactivated). "Inactivation" type inhibitors increase the percentage of receptors that are in an inactivated state.

In order to be maximally useful in treatment, it is also helpful to assess the side reactions which might occur. Thus, in addition to being able to modulate a particular calcium channel, it is desirable that the compound has very low activity with respect to the HERG $K^+$ channel which is expressed in the heart. Compounds that block this channel with high potency may cause reactions which are fatal. Thus, for a compound that modulates the calcium channel, it should also be shown that the HERG $K^+$ channel is not inhibited. Similarly, it would be undesirable for the compound to inhibit cytochrome p450 since this enzyme is required for drug detoxification. Finally, the compound will be evaluated for calcium ion channel type specificity by comparing its activity among the various types of calcium channels, and specificity for one particular channel type is preferred. The compounds which progress through these tests successfully are then examined in animal models as actual drug candidates.

The Invention Compounds

The substituents on the basic structures of formula (1) are described above. These include alkyl, alkenyl, alkynyl, etc., substituents.

As used herein, the term "alkyl," "alkenyl" and "alkynyl" include straight-chain, branched-chain and cyclic monovalent substituents, containing only C and H when they are unsubstituted or unless otherwise noted. Examples include methyl, ethyl, isobutyl, cyclohexyl, cyclopentylethyl, 2-propenyl, 3-butynyl, and the like. Typically, the alkyl, alkenyl and alkynyl substituents contain 1–10C (alkyl) or 2–12C (alkenyl or alkynyl). They may contain 1–6C (lower alkyl) or 2–6C (lower alkenyl or lower alkynyl), however, when the alkyl, alkenyl or alkynyl groups contain rings, they may contain as many as 18C, some of which may optionally be replaced by heteroatoms.

Heteroalkyl, heteroalkenyl and heteroalkynyl are similarly defined but may contain one or more O, S or N heteroatoms or combinations thereof within the backbone residue. In general, the terms alkyl, alkenyl and alkynyl include those wherein heteroatoms are contained when thus specified.

As used herein, "acyl" encompasses the definitions of alkyl, alkenyl, alkynyl, each of which is coupled to an additional residue through a carbonyl group. Heteroacyl includes the related heteroforms.

"Aromatic" moiety or "aryl" moiety refers to a monocyclic or fused bicyclic moiety such as phenyl or naphthyl which may also be heteroaromatic; "heteroaromatic" also refers to monocyclic or fused bicyclic ring systems containing one or more heteroatoms selected from O, S and N. The inclusion of a heteroatom permits inclusion of 5-membered rings as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Because tautomers are theoretically possible, phthalimido is also considered aromatic. Any monocyclic or fused ring bicyclic system which has the characteristics of aromaticity in terms of electron distribution throughout the ring system is included in this definition. Typically, the ring systems contain 5–12 ring member atoms.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1–8C, or the hetero forms thereof. These carbon chains may also include a carbonyl group, thus making them able to provide substituents as an acyl or heteroacyl moiety.

In general, any alkyl, alkenyl, alkynyl, acyl, or aryl group contained in a substituent may itself optionally be substituted by additional substituents. The nature of these substituents is similar to those recited with regard to the primary substituents themselves. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments. However, alkyl substituted by aryl, amino, alkoxy, and the like would be included.

Non-interfering substituents on aryl groups in general include, but are not limited to, optionally substituted alkyl, alkenyl, alkynyl, aryl, arylalkyl, and acyl, as well as halo, —CN, —CF$_3$, —NO, —NO$_2$, —OR, —NR$_2$, —SR, —SOR, —SO$_2$R, —OCOR, —NRCOR, —NRCONR$_2$, —NRCOOR, —OCONR$_2$, —RCO, —COOR, —NRSOR, —NRSO$_2$R, —SO$_3$R, —CONR$_2$, —SO$_2$NR$_2$, wherein each R is independently H or alkyl (1–8C), and the like.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Suitable pharmaceutically acceptable acids and bases are well-known in the art, i.e., acids such as hydrochloric, sulphuric, citric, acetic, or tartaric acids and bases such as potassium hydroxide, sodium hydroxide, ammonium hydroxide, caffeine, various amines, and the like. Methods for preparation of the appropriate salts are well-established in the art.

In addition, in some cases, the compounds of the invention contain one or more chiral centers. The invention includes the isolated stereoisomeric forms as well as mixtures of stereoisomers in varying degrees of chiral purity.

Synthesis of the Invention Compounds

The compounds of the invention modulate the activity of calcium channels; in general, said modulation is the inhibition of the ability of the channel to transport calcium. As described below, the effect of a particular compound on calcium channel activity can readily be ascertained in a routine assay whereby the conditions are arranged so that the channel is activated, and the effect of the compound on this activation (either positive or negative) is assessed. Typical assays are described hereinbelow.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Suitable pharmaceutically acceptable acids and bases are well-known in the art, such as hydrochloric, sulphuric, citric, acidic, or tartaric acids and potassium hydroxide, sodium hydroxide, ammonium hydroxide, caffeine, various amines, and the like. Methods for preparation of the appropriate salts are well-established in the art.

The compounds of the invention may be synthesized using conventional methods. Illustrative of such methods are Schemes 1 to 3.

Reaction Scheme 1 was used to prepare compounds P6–P8, P25, P30–P32, P36–P42 of the invention.

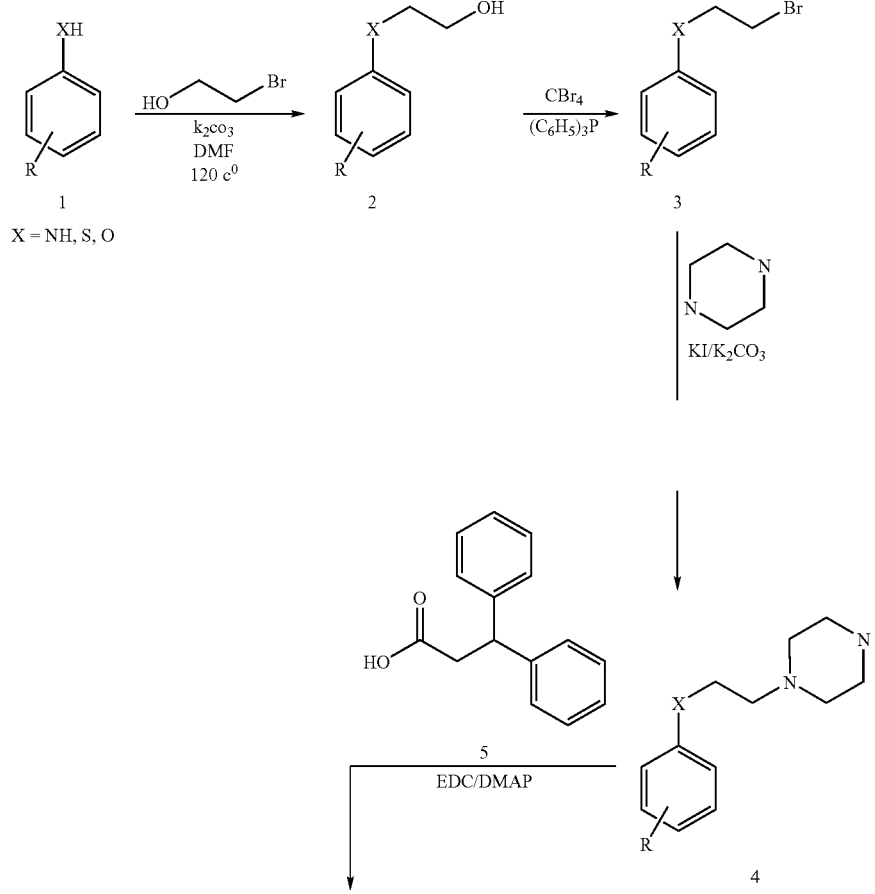

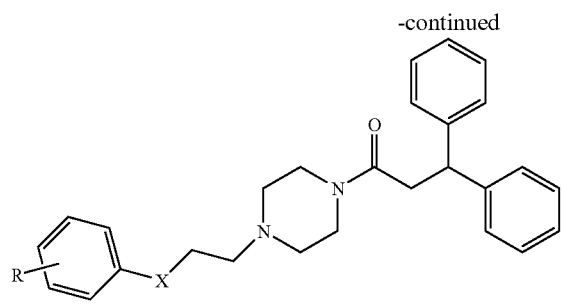
Reaction Scheme 2 was used to prepare compounds P9 and P10 of the invention.
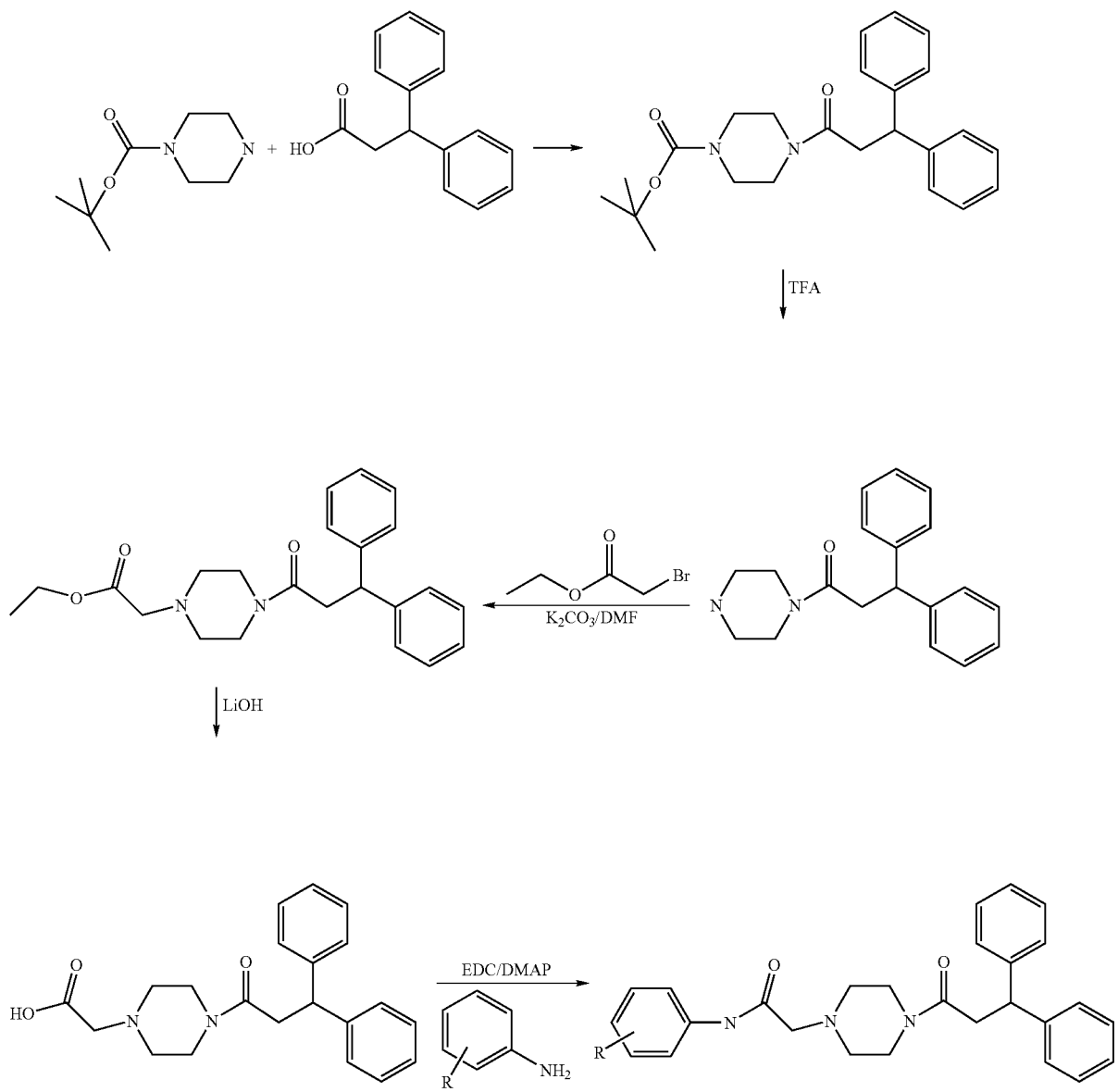

Reaction Scheme 3 was used to prepare compounds P1–P5, P12–P24, P27–P29, P33–P35 of the invention.

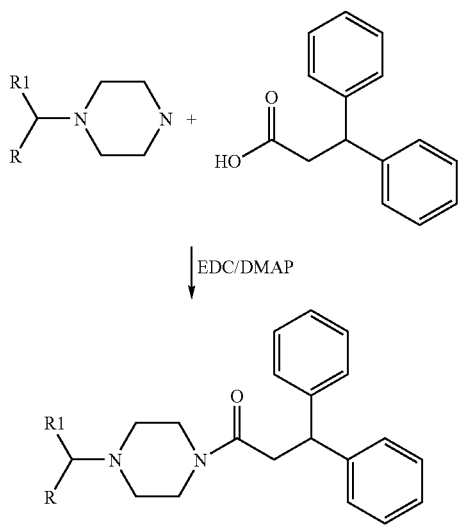

Reaction Scheme 3

Preferred Embodiments

The compounds of formula (1) are defined as shown in terms of the embodiments of their various substituents.

Particularly preferred embodiments of Formula (1) are those wherein only zero, one or two of the depicted rings are substituted and wherein the number of substituents on a single ring is three or less. Particularly preferred substituents for the phenyl rings shown include halo, especially fluoro or chloro; $CF_3$; optionally substituted, optionally heteroatom-containing alkyl, alkenyl, aryl, alkyl aryl, alkenyl aryl, phenoxy, and the like. Where the substituents on these moieties contain alkyl or aryl groups, these also may optionally be substituted. Also preferred are bridging substituents containing heteroatoms.

Particularly preferred substituents for the piperazine ring include =O, COOR, especially COOH and COOEt, alkyl, and alkenyl, (as defined above and optionally containing heteroatoms and all optionally substituted) and halo.

Preferred embodiments of X include unsubstituted alkyl or alkenyl, including embodiments wherein one or two carbons are replaced by N, S or O. Also preferred are embodiments wherein X is arylalkyl, especially wherein the aryl moiety is phenyl and wherein the alkyl moiety contains at least one heteroatom and/or is substituted by at least one =O. Also preferred are embodiments wherein X is alkyl and is in a cyclic form, and thus may contain up to 15C, wherein one or more of said C may optionally be replaced by a heteroatom. Also preferred are embodiments wherein X comprises a heteroaryl moiety, such as pyridyl, pyrimidyl, benzimidazole, benzothiazole and the like. Also preferred are embodiments wherein X is arylalkyl wherein the alkyl group is substituted by an aromatic or other cyclic moiety; especially preferred are those embodiments wherein the alkyl portion is methylene substituted by a cyclic moiety. Also preferred are embodiments wherein X is arylalkyl, the aryl portion is phenyl and is multiply substituted or is substituted by a substituent that comprises an additional aryl moiety.

Libraries and Screening

The compounds of the invention can be synthesized individually using methods known in the art per se, or as members of a combinatorial library.

Synthesis of combinatorial libraries is now commonplace in the art. Suitable descriptions of such syntheses are found, for example, in Wentworth, Jr., P., et al., *Current Opinion in Biol.* (1993) 9:109–115; Salemme, F. R., et al., *Structure* (1997) 5:319–324. The libraries contain compounds with various substituents and various degrees of unsaturation, as well as different chain lengths. The libraries, which contain, as few as 10, but typically several hundred members to several thousand members, may then be screened for compounds which are particularly effective against a specific subtype of calcium channel, i.e., the N-type channel. In addition, using standard screening protocols, the libraries may be screened for compounds which block additional channels or receptors such as sodium channels, potassium channels and the like.

Methods of performing these screening functions are well known in the art. These methods can also be used for individually ascertaining the ability of a compound to agonize or antagonize the channel. Typically, the channel to be targeted is expressed at the surface of a recombinant host cell such as human embryonic kidney cells. The ability of the members of the library to bind the channel to be tested is measured, for example, by the ability of the compound in the library to displace a labeled binding ligand such as the ligand normally associated with the channel or an antibody to the channel. More typically, ability to antagonize the channel is measured in the presence of calcium ion and the ability of the compound to interfere with the signal generated is measured using standard techniques. In more detail, one method involves the binding of radiolabeled agents that interact with the calcium channel and subsequent analysis of equilibrium binding measurements including, but not limited to, on rates, off rates, $K_d$ values and competitive binding by other molecules.

Another method involves the screening for the effects of compounds by electrophysiological assay whereby individual cells are impaled with a microelectrode and currents through the calcium channel are recorded before and after application of the compound of interest.

Another method, high-throughput spectrophotometric assay, utilizes loading of the cell lines with a fluorescent dye sensitive to intracellular calcium concentration and subsequent examination of the effects of compounds on the ability of depolarization by potassium chloride or other means to alter intracellular calcium levels.

As described above, a more definitive assay can be used to distinguish inhibitors of calcium flow which operate as open channel blockers, as opposed to those that operate by promoting inactivation of the channel. The methods to distinguish these types of inhibition are more particularly described in the examples below. In general, open-channel blockers are assessed by measuring the level of peak current when depolarization is imposed on a background resting potential of about −100 mV in the presence and absence of the candidate compound. Successful open-channel blockers will reduce the peak current observed and may accelerate the decay of this current. Compounds that are inactivated channel blockers are generally determined by their ability to shift the voltage dependence of inactivation towards more negative potentials. This is also reflected in their ability to reducepeak currents at more depolarized holding potentials (e.g., −70 mV) and at higher frequencies of stimulation, e.g., 0.2 Hz vs. 0.03 Hz.

Utility and Administration

For use as treatment of human and animal subjects, the compounds of the invention can be formulated as pharmaceutical or veterinary compositions. Depending on the subject to be treated, the mode of administration, and the type of treatment desired—e.g., prevention, prophylaxis, therapy; the compounds are formulated in ways consonant with these parameters. A summary of such techniques is found in *Remington's Pharmaceutical Sciences,* latest edition, Mack Publishing Co., Easton, Pa., incorporated herein by reference.

In general, for use in treatment, the compounds of formula (1) may be used alone, as mixtures of two or more compounds of formula (1) or in combination with other pharmaceuticals. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as in understood in the art.

For administration to animal or human subjects, the dosage of the compounds of the invention is typically 0.1–15 mg/kg, preferably 0.1–1 mg/kg. However, dosage levels are highly dependent on the nature of the condition, the condition of the patient, the judgment of the practitioner, and the frequency and mode of administration.

The following examples are intended to illustrate but not to limit the invention.

EXAMPLE 1

Synthesis of 1-{4-[2-(2,4-difluoro-phenoxy)-ethyl]-piperazin-1-yl}-3,3-diphenyl-propan-1-one

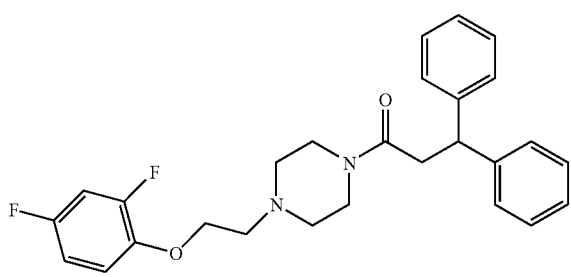

A. Synthesis of 2-(2,4-difluoro-phenoxy)-ethanol

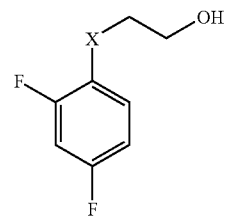

$K_2CO_3$ (1.07 g, 7.78 mmol) was added to a solution of 2,4-difluoro phenol (0.84 g, 6.48 mmol) in dry DMF (15 ml). 2-Bromoethanol (0.81 g, 6.48 mmol) was added, and the mixture was heated overnight at 120° C. The mixture was cooled, taken up in EtOAc, extracted with water (20 ml), saturated NaCl (4×20 ml), dried over $MgSO_4$, and evaporated under reduced pressure. The product was purified by column chromatography on silica (Hexane:EtOAc 3:1) to give the desired product in 63% yield B. Synthesis of 4-(2-bromo-ethoxy)-1,3-difluoro benzene

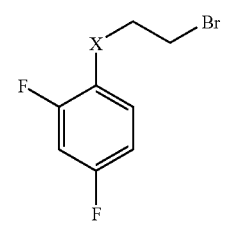

To a cool solution 2-(2,4-difluoro-phenoxy)-ethanol (0.48 g, 2.77 mmol.) in $CH_2Cl_2$ (15 ml), triphenyl phosphine (1.3 g, 5 mmol)) was added. Carbon tetrabromide (1.65 g, 5 mmol.) in $CH_2Cl_2$ (3 ml) was added to the solution dropwise under $N_2$. The solution was stirred for 30 minutes. EtOAc was added, then the solvent was evaporated under reduced pressure.

The product was purified by column chromatography on silica (Hexane:EtOAc 1:1) to give the desired product in 83% yield.

C. Synthesis of 1-[2-(2,4-difluoro-phenoxy)-ethyl]-piperazine

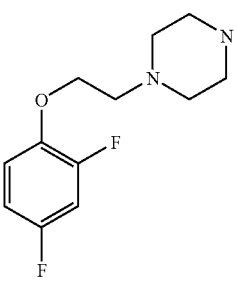

A mixture of piperazine (8.7 g, 101.26 mmol) in butanone (70 ml), 4-(2-bromo-ethoxy)-1,3-difluoro benzene (6.0 g, 25.31 mmol), anhydrous K$_2$CO$_3$ (3.5 g, 25.31 mmol) and KI (4.2 g, 25.31 mmol) was refluxed under nitrogen for 18 hours. The mixture was then cooled and filtered and the solvent removed in vacuo. The residue was dissolved in CH$_2$Cl$_2$ (200 ml) and washed with water (50 ml). Drying and removal of the solvent followed by chromatography (CH$_2$Cl$_2$:CH$_3$OH:NH$_4$OH 10:1) afforded desired product in 73% yield.

To a solution of 1-[2-(2,4-difluoro-phenoxy)-ethyl]-piperazine (1.0 g, 4.13 mmol) in dry CH$_2$Cl$_2$ (30 ml) was added 3,3-diphenylpropanoic acid (1.12 g, 4.95 mmol) under nitrogen. To the reaction was added EDC (1.0 g, 5.36 mmol) and DMAP (cat) and the reaction mixture stirred under nitrogen at room temperature overnight. The reaction was then concentrated under reduced pressure. The residue dissolved in ethyl acetate:water (10:1) (150 ml). The organic was washed with water (30 ml, 2×) and 10% NaOH (30 ml) and dried over MgSO$_4$ and evaporated to dryness. The resulting residue was purified by column chromatography using ethyl acetate to give desired product in 85% yield.

EXAMPLE 2

Synthesis of N-(2,6-dimethyl-phenyl)-2-[4-(3,3-diphenyl-propionyl)-piperazin-1-yl]-acetamide

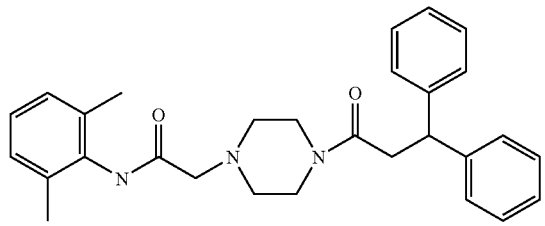

A. Synthesis of 4-(3,3-diphenyl-propionyl)-piperazine-1-carboxylic acid tert-butyl ester

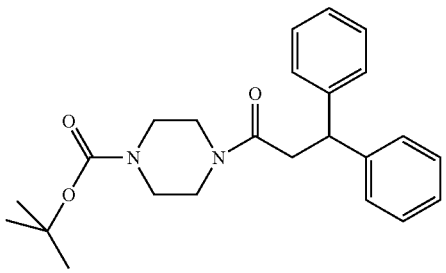

To a solution of 3,3 diphenylpropionic acid (1.45 g, 6.44 mmol) in dry CH$_2$Cl$_2$ (70 ml) was added mono-boc piperizine (1.32 g, 7.08 mmol) under nitrogen. To the reaction was added EDC (2.71 g, 14.16 mmol) and DMAP (cat) and the reaction mixture stirred under nitrogen at room temperature overnight. The reaction was then concentrated under reduced pressure. The residue dissolved in ethyl acetate:water (10:1) (200 ml). The organic was washed with water (50 ml, 2×) and 10% NaOH (50 ml) and dried over MgSO$_4$ and evaporated to dryness. The resulting residue was purified by column chromatography using hexane:ethyl acetate (1:1) to give desired product in 76% yield.

B. Synthesis of 3,3-diphenyl-1-piperazin-1-yl-propan-1-one

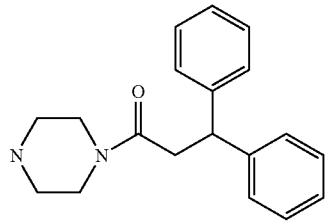

To a solution of 4-(3,3-diphenyl-propionyl)-piperazine-1-carboxylic acid tert-butyl ester (2.15 g, 5.45 mmol) in dry CH$_2$Cl$_2$ (60 ml) was added TFA (20 ml) and resulting mixture stirred at room temperature for 3 hrs. Solvent and excess TFA was then evaporated and the residue was dissolved in CH$_2$Cl$_2$ (150 ml) and washed with sat. NaHCO$_3$ (2×) and dried over MgSO$_4$. Evaporation of solvent gave 1.65 g of pure product.

C. Synthesis of [4-(3,3-diphenyl-propionyl)-piperazin-1-yl]-acetic acid ethyl ester

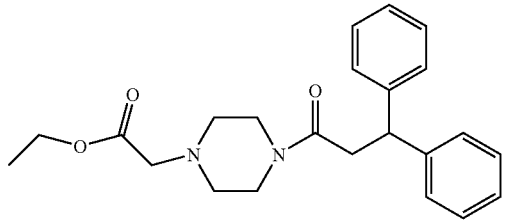

To a solution of 3,3-diphenyl-1-piperazin-1-yl-propan-1-one (2.0 g, 6.79 mmol) and ethyl bromoacetate (0.94 ml, 8.49 mmol) in dry DMF (15 ml) was added K$_2$CO$_3$ (2.7 g, 19.53 mmol) and the mixture was heated to 70° C. overnight. Reaction mixture was cooled and water (32 ml) was added. The product was extracted with ether, dried and evaporated. The residue was purified by column chromatography using hexane:ethyl acetate (1:4) to give the desired product in 60% yield.

D. Synthesis of [4-(3,3-diphenyl-propionyl)-piperazin-1-yl]-acetic acid

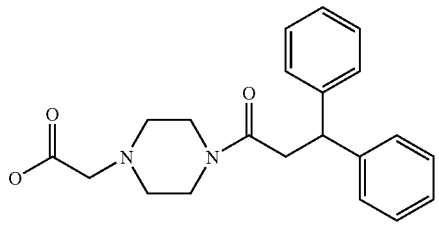

A mixture of [4-(3,3-diphenyl-propionyl)-piperazin-1-yl]-acetic acid ethyl ester (1.17 g, 3.07 mmol) and LiOH (645 mg, 15.35 mmol) in MeOH: H$_2$O (3:1, 40 ml) stirred at room temperature for 2 days. The solvent was then evaporated and residue dissolved in water. Upon acidified with 2N HCl to pH 3, product precipitated in aq. phase, filtered and washed few times with water and dried to give the desired product in 78% yield.

To a solution of [4-(3,3-diphenyl-propionyl)-piperazin-1-yl]-acetic acid (0.8 g, 2.29 mmol) in dry $CH_2Cl_2$ (50 ml) was added 2,6-dimethyl aniline (0.28 ml, 2.29 mmol) under nitrogen. To the reaction was added EDC (0.87 g, 4.58 mmol) and DMAP (cat) and the reaction mixture stirred under nitrogen at room temperature overnight. The reaction was then concentrated under reduced pressure. The residue dissolved in ethyl acetate:water (10:1) (120 ml). The organic was washed with water (30ml, 2×) and 10% NaOH (30 ml) and dried over $MgSO_4$ and evaporated to dryness. The resulting residue was purified by column chromatography using $CH_2Cl_2$:MeOH (15:1) to give desired product in 72% yield.

EXAMPLE 3

Synthesis of 1-[4-(1-methyl-piperidin-4-ylmethyl) piperazin-1-yl]-3,3-diphenyl-propan-1-one

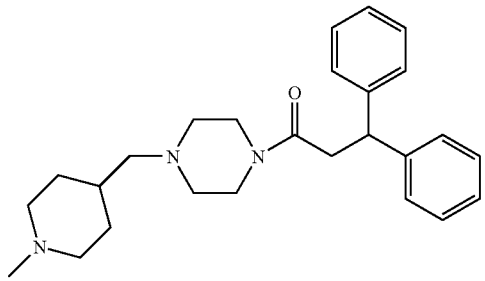

To a solution of 1-(1-methyl-piperidin-4ylmethyl)-piperazine (0.25 g, 1.26 mmol) in dry $CH_2Cl_2$ (25 ml) was added 3,3-diphenylpropanoic acid (0.26 g, 1.15 mmol) under nitrogen. To the reaction was added EDC (0.48 g, 2.53 mmol) and DMAP (cat) and the reaction mixture stirred under nitrogen at room temperature overnight. The reaction was then concentrated under reduced pressure. The residue dissolved in ethyl acetate:water (10:1) (100 ml). The organic was washed with water (25 ml, 2×) and 10% NaOH (25 ml) and dried over $MgSO_4$ and evaporated to dryness. The resulting residue was purified by column chromatography using $CH_2Cl_2$:MeOH (5:1) to give desired product in 69% yield.

EXAMPLE 4

N-type Calcium Channel Blocking Activities of Various Invention Compounds

The methods of Example 1 were followed with slight modifications as will be apparent from the description below.

A. Transformation of HEK Cells:

N-type calcium channel blocking activity was assayed in human embryonic kidney cells, HEK 293, stably transfected with the rat brain N-type calcium channel subunits ($\alpha_{1B}$+$\alpha_{2\delta}$+$\beta_{1b}$ cDNA subunits). Alternatively, N-type calcium channels ($\alpha_{1B}$+$\alpha_{2\delta}$+$\beta_{1b}$ cDNA subunits), L-type channels ($\alpha_{1C}$+$\alpha_{2\delta}$+$\beta_{1b}$ cDNA subunits) and P/Q-type channels ($\alpha_{1A}$+$\alpha_{2\delta}$+$\beta_{1b}$ cDNA subunits) were transiently expressed in HEK 293 cells. Briefly, cells were cultured in Dulbecco's modified eagle medium (DMEM) supplemented with 10% fetal bovine serum, 200 U/ml penicillin and 0.2 mg/ml streptomycin at 37° C. with 5% $CO_2$. At 85% confluency cells were split with 0.25% trypsin/1 mM EDTA and plated at 10% confluency on glass coverslips. At 12 hours the medium was replaced and the cells transiently transfected using a standard calcium phosphate protocol and the appropriate calcium channel cDNAs. Fresh DMEM was supplied and the cells transferred to 28° C./5% $CO_2$. Cells were incubated for 1 to 2 days to whole cell recording.

B. Measurement of Inhibition:

Whole cell patch clamp experiments were performed using an Axopatch 200B amplifier (Axon Instruments, Burlingame, Calif.) linked to a personal computer equipped with pCLAMP software. The external and internal recording solutions contained, respectively, 5 mM $BaCl_2$, 1 mM $MgCl_2$, 10 mM HEPES, 40 mM TEACl, 10 mM glucose, 87.5 mM CsCl (pH 7.2) and 108 mM CsMS, 4 mM $MgCl_2$, 9 mM EGTA, 9 mM HEPES (pH 7.2). Currents were typically elicited from a holding potential of −80 mV to +10 mV using Clampex software (Axon Instruments). Typically, currents were first elicited with low frequency stimulation (0.03 Hz) and allowed to stabilize prior to application of the compounds. The compounds were then applied during the low frequency pulse trains for two to three minutes to assess tonic block, and subsequently the pulse frequency was increased to 0.2 Hz to assess frequency dependent block. Data were analyzed using Clampfit (Axon Instruments) and SigmaPlot 4.0 (Jandel Scientific).

Using the procedure set forth in this Example 4, various compounds of the invention were tested for their ability to block N-type calcium channels. The results show $IC_{50}$ values in the range of 0.05–1 µM, as shown in Table 1.

TABLE 1

Block of α1B N-type Channels

| Compound | 0.067 Hz IC50 (µM) | 0.2 Hz IC50 (µM) |
| --- | --- | --- |
| P1 | 0.240 | 0.320 |
| P2 | 0.387 | 0.292 |
| P3 | 0.531 | 0.445 |
| P6 | 0.520 | 0.360 |
| P7 | 1.090 | 0.800 |
| P9 | >1 | >1 |
| P10 | 0.471 | 0.295 |
| P11 | 0.660 | 0.480 |
| P12 | 0.350 | 0.288 |
| P13 | 0.554 | 0.413 |
| P14 | 0.261 | 0.217 |
| P15 | 0.534 | 0.321 |
| P16 | 0.500 | 0.300 |
| P17 | 0.376 | 0.224 |
| P18 | 0.110 | 0.076 |
| P19 | 0.280 | 0.180 |
| P20 | 0.430 | 0.240 |
| P21 | 0.370 | 0.290 |
| P22 | 0.314 | 0.174 |
| P23 | 0.650 | 0.410 |
| P24 | 0.190 | 0.130 |
| P25 | 0.421 | 0.275 |
| P26 | 0.263 | 0.130 |
| P27 | 0.715 | 0.371 |
| P28 | 0.249 | 0.159 |
| P29 | 0.361 | 0.298 |
| P30 | 3.55 | 0.601 |
| P31 | 0.597 | 0.398 |
| P32 | 0.313 | 0.266 |
| P33 | 0.240 | 0.180 |

TABLE 1-continued

Block of α1B N-type Channels

| Compound | 0.067 Hz<br>IC50 (μM) | 0.2 Hz<br>IC50 (μM) |
|---|---|---|
| P34 | 0.290 | 0.150 |
| P35 | 0.520 | 0.430 |
| P36 | 0.450 | 0.350 |
| P37 | 0.670 | 0.420 |
| P38 | 0.183 | 0.135 |
| P39 | 0.400 | 0.280 |
| P40 | 0.364 | 0.308 |
| P41 | 0.349 | 0.282 |

EXAMPLE 5

Assessment of Selective Calcium Channel Blocking Activity

Antagonist activity was measured using whole cell patch recordings on human embryonic kidney cells either stably or transiently expressing rat $\alpha_{1B}+\alpha_{2b}+\beta_{1b}$ channels (N-type channels) with 5 mM barium as a charge carrier.

For transient expression, host cells, such as human embryonic kidney cells, HEK 293 (ATCC# CRL 1573) were grown in standard DMEM medium supplemented with 2 mM glutamine and 10% fetal bovine serum. HEK 293 cells were transfected by a standard calcium-phosphate-DNA coprecipitation method using the rat $\alpha_{1B}+\beta_{1b}+\alpha_{2}\delta$ N-type calcium channel subunits in a vertebrate expression vector (for example, see *Current Protocols in Molecular Biology*).

After an incubation period of from 24 to 72 hrs the culture medium was removed and replaced with external recording solution (see below). Whole cell patch clamp experiments were performed using an Axopatch 200B amplifier (Axon Instruments, Burlingame, Calif.) linked to an IBM compatible personal computer equipped with pCLAMP software. Borosilicate glass patch pipettes (Sutter Instrument Co., Novato, Calif.) were polished (Microforge, Narishige, Japan) to a resistance of about 4 MΩ when filled with cesium methanesulfonate internal solution (composition in MM: 109 $CsCH_3SO_4$, 4 $MgCl_2$, 9 EGTA, 9 HEPES, pH 7.2). Cells were bathed in 5 mM $Ba^{++}$ (in mM: 5 $BaCl_2$, 1 $MgCl_2$, 10 HEPES, 40 tetraethylammonium chloride, 10 glucose, 87.5 CsCl pH 7.2). Current data shown were elicited by a train of 100 ms test pulses at 0.066 Hz from −100 mV and/or −80 mV to various potentials (min. −20 mV, max. +30 mV). Drugs were perfused directly into the vicinity of the cells using a microperfusion system.

Normalized dose-response curves were fit (Sigmaplot 4.0, SPSS Inc., Chicago, Ill.) by the Hill equation to determine $IC_{50}$ values. Steady-state inactivation curves were plotted as the normalized test pulse amplitude following 5 s inactivating prepulses at +10 mV increments. Inactivation curves were fit (Sigmaplot 4.0) with the Boltzman equation, $I_{peak}$ (normalized)=$1/(1+\exp((V-V_h)z/25.6))$, where V and $V_h$ are the conditioning and half inactivation potentials, respectively, and z is the slope factor.

Figure 3:
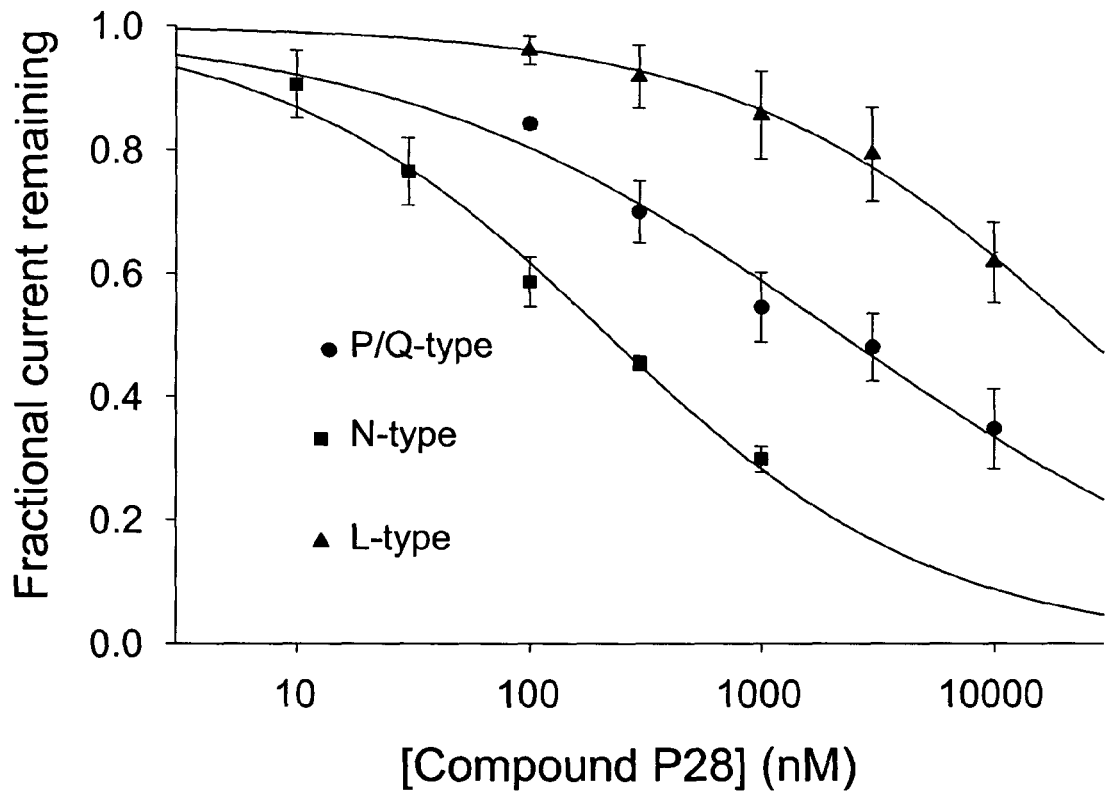

Table 2 shows the results obtained with several compounds of the invention which are selective for N-type channels. In addition, FIGS. 2 and 3 show the specificity of compounds P24 and P28 of the invention which selectively block N-type channels.

TABLE 2

Selectivity of Compounds for N-type $Ca^{2+}$ Channels Tested at 0.1 Hz, 5 mM $Ba^{2+}$

| Compound | N-type<br>$IC_{50}$<br>(μM) | P/Q-type<br>$IC_{50}$<br>(μM) | L-type<br>$IC_{50}$<br>(μM) | P/Q:N ratio | L:N ratio |
|---|---|---|---|---|---|
| P24 | 0.257 | 2.449 | ~30 | 9.5:1 | 117:1 |
| P28 | 0.214 | 6.446 | 20 | 9.5:1 | 93:1 |

EXAMPLE 6

Block of $\alpha_{1G}$ T-Type Channels

Standard patch-clamp techniques were employed to identify blockers of T-type currents. Briefly, previously described HEK cell lines stably expressing human $\alpha_{1G}$ subunits were used for all the recordings (passage #: 4–20, 37° C., 5% $CO_2$). To obtain T-type currents, plastic dishes containing semi-confluent cells were positioned on the stage of a ZEISS AXIOVERT S100 microscope after replacing the culture medium with external solution (see below). Whole-cell patches were obtained using pipettes (borosilicate glass with filament, O.D.: 1.5 mm, I.D.: 0.86 mm, 10 cm length), fabricated on a SUTTER P-97 puller with resistance values of ~5 MΩ (see below for internal medium).

TABLE 3

External Solution 500 ml - pH 7.4, 265.5 mOsm

| Salt | Final mM | Stock M | Final ml |
|---|---|---|---|
| CsCl | 132 | 1 | 66 |
| $CaCl_2$ | 2 | 1 | 1 |
| $MgCl_2$ | 1 | 1 | 0.5 |
| HEPES | 10 | 0.5 | 10 |
| glucose | 10 | — | 0.9 grams |

TABLE 4

Internal Solution 50 ml - pH 7.3 with CsOH, 270 mOsm

| Salt | Final mM | Stock M | Final ml |
|---|---|---|---|
| Cs-Methanesulfonate | 108 | — | 1.231 gr/50 ml |
| $MgCl_2$ | 2 | 1 | 0.1 |
| HEPES | 10 | 0.5 | 1 |
| EGTA-Cs | 11 | 0.25 | 2.2 |
| ATP | 2 | 0.2 | 0.025<br>(1 aliquot/2.5 ml) |

T-type currents were reliably obtained by using two voltage protocols:
(1) "non-inactivating", and
(2) "inactivation"

In the non-inactivating protocol, the holding potential is set at −110 mV and with a pre-pulse at −100 mV for 1 second prior to the test pulse at −40 mV for 50 ms. In the inactivation protocol, the pre-pulse is at approximately −85 mV for 1 second, which inactivates about 15% of the T-type channels.

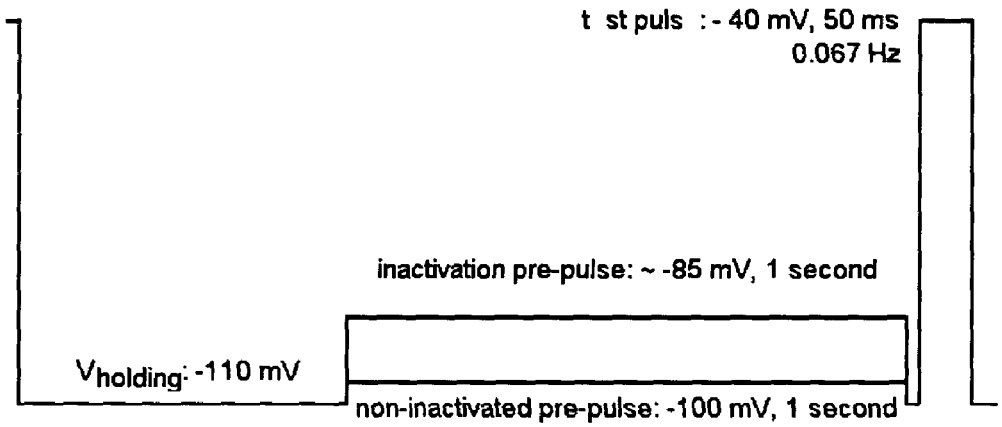

Test compounds were dissolved in external solution, 0.1–0.01% DMSO. After ~10 min rest, they were applied by gravity close to the cell using a WPI microfil tubing. The "non-inactivated" pre-pulse was used to examine the resting block of a compound. The "inactivated" protocol was employed to study voltage-dependent block. However, the initial data shown below were mainly obtained using the non-inactivated protocol only. $IC_{50}$ values are shown for various compounds of the invention in Table 5.

TABLE 5

Block of $\alpha_{1G}$ T-type Channels

| Compound | −100 mV IC50 (μM) | −80 mV IC50 (μM) |
|---|---|---|
| P19 | 0.154 | |
| P21 | No effect | |
| P23 | 0.905 | |
| P30 | No effect | |
| P33 | 0.0088 | 0.0022 |
| P41 | No effect | |

The invention claimed is:

1. A compound of the formula:

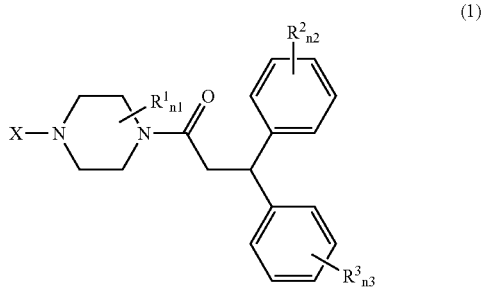

(1)

or the salt or stereoisomeric forms thereof,
wherein each $R^1$–$R^3$ is independently a non-interfering substituent; and
wherein a combination of $R^2$ and $R^3$ may form a bridge between phenyl groups, which may be a bond or a $CR_2$ group, an NR group, O, or S wherein the S is optionally oxidized;
$n^1$ is 0–4 and $n^2$ and $n^3$ are independently 0–5; and
wherein X is selected from the group consisting of:
(a) alkyl (1–12C) or alkenyl (2–12C) optionally including one or more N, O or S with the proviso that any N included in a ring is secondary or is tertiary solely because of an alkyl substitution;
(b) aryl, provided that if aryl is phenyl or pyridyl, said aryl must contain at least one substituent and wherein if said aryl is phenyl and contains only one substituent, said substituent must comprise an aryl group or a trialkylsilyl group and wherein said phenyl is not 2,3-dimethylphenyl or fused to an aliphatic ring;
(c) —CRH-aryl wherein R is H, alkyl, or a heteroaromatic ring, wherein when R is H, aryl is optionally substituted 4-pyridyl, or is substituted phenyl other than phenyl fused to an aliphatic ring, or is substituted naphthyl or is substituted 5-membered aryl; and
(d) -alkylene-aryl wherein said alkylene contains at least 2 C, and further optionally contains one heteroatom and/or is substituted by =O and/or OH provided that if said alkylene is $CH_2CH_2$, $CH_2CH_2CH_2$, $CH_2CH_2O$ or $CH_2CH_2CH_2O$, and said aryl is phenyl, said phenyl must be substituted; and if said alkylene is $CH_2CH_2CH_2O$ substituted by OH, said aryl is other than substituted quinolyl or monosubstituted phenyl.

2. The compound of claim 1, wherein each $R^1$–$R^3$ is independently halo, NO, $NO_2$, CN, $SO_2H$, $SO_3H$, optionally substituted alkyl (1–12C), alkenyl (2–12C), alkynyl (2–12C), aryl (6–12C) or arylalkyl, arylalkenyl or arylalkynyl (each 7–16C) wherein in each of the foregoing 1–4C may be replaced by a heteroatom (Si, N, O and/or S) and wherein said optional substituents may include =O and wherein when alkyl, alkenyl, or alkynyl comprises at least one cyclic moiety, the number of C contained may be up to and including 18, wherein one or more C may be replaced by a heteroatom, and
wherein two substituents at adjacent positions on the same ring may form a 3–7 membered saturated or unsaturated ring fused to said substituted ring, said fused ring is optionally itself substituted and optionally contains one or more heteroatoms (N, S, O), and
wherein $R^1$ may be keto.

3. The compound of claim 1, wherein X is alkyl (1–12C) or alkenyl (2–12C) optionally including one or more N, O or S with the proviso that any N included in a ring is secondary or is tertiary solely because of an alkyl substitution.

4. The compound of claim 3, wherein X is acyclic.

5. The compound of claim 1, wherein X is aryl, provided that if aryl is phenyl or pyridyl, said aryl must contain at least one substituent and wherein if said aryl is phenyl and contains only one substituent, said substituent must comprise an aryl group or a trialkylsilyl group and wherein said phenyl is not 2,3-dimethylphenyl or fused to an aliphatic ring.

6. The compound of claim 5, wherein X is benzimidazole, benzothiazole, or substituted phenyl.

7. The compound of claim 1, wherein —CRH-aryl wherein R is H, alkyl, or a heteroaromatic ring, wherein when R is H, aryl is optionally substituted 4-pyridyl, or is substituted phenyl other than phenyl fused to an aliphatic ring, or is substituted naphthyl or is substituted 5-membered aryl.

8. The compound of claim 7, wherein R is cyclopropyl or a thiophene residue.

9. The compound of claim 1, wherein X is -alkylene-aryl wherein said alkylene contains at least 2 C, and further optionally contains one heteroatom and/or is substituted by =O and/or OH provided that if said alkylene is $CH_2CH_2$, $CH_2CH_2CH_2$, $CH_2CH_2O$ or $CH_2CH_2CH_2O$, and said aryl is phenyl, said phenyl must be substituted; and if said alkylene is $CH_2CH_2CH_2O$ substituted by OH, said aryl is other than substituted quinolyl or monosubstituted phenyl.

10. The compound of claim 9, wherein said alkylene comprises a keto substituent.

11. The compound of claim 9, wherein X is substituted phenyl coupled to $(CH_2)_n$ or through a bond to Y to $Y(CH_2)_n$, wherein n is 2–5, and Y is NH, O or S.

12. The compound of claim 1, wherein at least one of n1–n3 is 0.

13. The compound of claim 1, wherein n1 is 0 or $R^1$ is alkyl.

14. The compound of claim 1, wherein both n2 and n3 are 0.

15. The compound of claim 1, wherein all of n1–n3 are 0.

16. The compound of claim 1 which is
1-{4-[4-(4-Fluoro-benzyl)-phenyl]-piperazin-1-yl}-3,3-diphenyl-propan-1-one;

1-[4-(3,5-Di-tert-butyl-4-hydroxy-benzyl)-piperazin-1-yl]-3,3-diphenyl-propan-1-one;
1-{4-[3-(4-Amino-2,3,5-trimethyl-phenoxy)-2-hydroxy-propyl]-piperazin-1-yl}-3,3-diphenyl-propan-1-one;
1-(4-Adamantan-1-ylmethyl-piperazin-1-yl)-3,3-diphenyl-propan-1-one;
1-(4-Benzothiazol-2-yl-piperazin-1-yl)-3,3-diphenyl-propan-1-one;
3,3-Diphenyl-1-{4-[2-(3,4,5-trimethoxy-phenoxy)-ethyl]-piperazin-1-yl}-propan-1-one;
1-{4-[2-(3,4-Dimethoxy-phenoxy)-ethyl]-piperazin-1-yl}-3,3-diphenyl-propan-1-one;
1-{4-[2-(Benzothiazol-2-ylsulfanyl)-ethyl]-piperazin-1-yl}-3,3-diphenyl-propan-1-one;
N-(2,6-Dimethyl-phenyl)-2-[4-(3,3-diphenyl-propionyl)-piperazin-1-yl]-acetamide;
2-[4-(3,3-Diphenyl-propionyl)-piperazin-1-yl]-N-methyl-N-phenyl-acetamide;
3,3-Diphenyl-1-[4-(1-phenyl-ethyl)-piperazin-1-yl]-propan-1-one;
1-[4-(2-Diallylamino-ethyl)-piperazin-1-yl]-3,3-diphenyl-propan-1-one;
1-[4-(2-Dipropylamino-ethyl)-piperazin-1-yl]-3,3-diphenyl-propan-1-one;
1-(4-sec-Butyl-piperazin-1-yl)-3,3-diphenyl-propan-1-one;
1-[4-(1-Ethyl-propyl)-piperazin-1-yl]-3,3-diphenyl-propan-1-one;
1-[4-(1-Methyl-piperidin-3-ylmethyl)-piperazin-1-yl]-3,3-diphenyl-propan-1-one;
1-(4-Heptyl-piperazin-1-yl)-3,3-diphenyl-propan-1-one;
3,3-Diphenyl-1-(4-pyridin-4-ylmethyl-piperazin-1-yl)-propan-1-one;
1-[4-(3,5-Dichloro-phenyl)-piperazin-1-yl]-3,3-diphenyl-propan-1-one;
1-(4-Cycloheptyl-piperazin-1-yl)-3,3-diphenyl-propan-1-one;
1-[4-(3,4-Dimethyl-phenyl)-piperazin-1-yl]-3,3-diphenyl-propan-1-one;
1-(4-Biphenyl-4-yl-piperazin-1-yl)-3,3-diphenyl-propan-1-one;
1-[4-(2,3-Dichloro-phenyl)-piperazin-1-yl]-3,3-diphenyl-propan-1-one;
1-[4-(1-Methyl-piperidin-4-ylmethyl)-piperazin-1-yl]-3,3-diphenyl-propan-1-one;
N-{2-[4-(3,3-Diphenyl-propionyl)-piperazin-1-yl]-ethyl}-3,4,5-trimethoxy-benzamide;
1-(4-Isopropyl-piperazin-1-yl)-3,3-diphenyl-propan-1-one;
1-[4-(3-Dimethylamino-propyl)-piperazin-1-yl]-3,3-diphenyl-propan-1-one;
3,3-Diphenyl-1-[4-(4-trimethylsilanyl-phenyl)-piperazin-1-yl]-propan-1-one;
3,3-Diphenyl-1-[4-(2-phenylamino-ethyl)-piperazin-1-yl]-propan-1-one;
1-{4-[2-(2,4-Difluoro-phenoxy)-ethyl]-piperazin-1-yl}-3,3-diphenyl-propan-1-one;
3,3-Diphenyl-1-{4-[2-(2,3,5,6-tetrafluoro-phenoxy)-ethyl]-piperazin-1-yl}-propan-1-one;
1-[4-(1-Benzyl-1H-benzoimidazol-2-yl)-piperazin-1-yl]-3,3-diphenyl-propan-1-one;
3,3-Diphenyl-1-[4-(phenyl-thiophen-2-yl-methyl)-piperazin-1-yl]-propan-1-one;
1-{4-[Cyclopropyl-(4-fluoro-phenyl)-methyl]-piperazin-1-yl}-3,3-diphenyl-propan-1-one;
(4-{2-[4-(3,3-Diphenyl-propionyl)-piperazin-1-yl]-ethoxy}-2,3,6-trimethyl-phenyl)-carbamic acid tert-butyl ester;
1-{4-[2-(4-Amino-2,3,5-trimethyl-phenoxy)-ethyl]-piperazin-1-yl}-3,3-diphenyl-propan-1-one;
1-{4-[2-(4-Methoxy-phenoxy)-ethyl]-piperazin-1-yl}-3,3-diphenyl-propan-1-one;
1-{4-[2-(Benzo[1,3]dioxol-5-yloxy)-ethyl]-piperazin-1-yl}-3,3-diphenyl-propan-1-one;
1-{4-[2-(2,4-Dichloro-phenoxy)-ethyl]-piperazin-1-yl}-3,3-diphenyl-propan-1-one;
1-{4-[2-(4-Fluoro-phenoxy)-ethyl]-piperazin-1-yl}-3,3-diphenyl-propan-1-one; or
3,3-Diphenyl-1-[4-(2-phenylsulfanyl-ethyl)-piperazin-1-yl]-propan-1-one;

or a salt thereof.

17. A pharmaceutical composition for use in treating conditions characterized by abnormal calcium channel activity which composition comprises, in admixture with a pharmaceutically acceptable excipient, a dosage amount of at least one compound of claim 1.

18. A method to treat conditions associated with abnormal calcium channel activity in a subject which method comprises administering to a subject in need of such treatment at least one compound of claim 1 or a pharmaceutical composition thereof.

* * * * *